US008090562B2

(12) United States Patent
Snider et al.

(10) Patent No.: US 8,090,562 B2
(45) Date of Patent: Jan. 3, 2012

(54) PREDICTING RISK OF MAJOR ADVERSE CARDIAC EVENTS

(75) Inventors: James V. Snider, Pleasanton, CA (US); Eugene R. Heyman, Montgomery, MD (US)

(73) Assignee: Critical Care Diagnostics, Inc., New York, NY (US)

( * ) Notice: Subject to any disclaimer, the term of this patent is extended or adjusted under 35 U.S.C. 154(b) by 284 days.

(21) Appl. No.: 12/425,956

(22) Filed: Apr. 17, 2009

(65) Prior Publication Data

US 2009/0264779 A1 Oct. 22, 2009

Related U.S. Application Data

(60) Provisional application No. 61/046,158, filed on Apr. 18, 2008.

(51) Int. Cl.
*G06G 7/58* (2006.01)
(52) U.S. Cl. ............. 703/11; 702/19; 435/6.1; 530/350
(58) Field of Classification Search .................. None
See application file for complete search history.

(56) References Cited

U.S. PATENT DOCUMENTS

| | | | |
|---|---|---|---|
| 5,786,163 | A | 7/1998 | Hall |
| 6,040,147 | A | 3/2000 | Ridker et al. |
| 6,210,976 | B1 | 4/2001 | Sabbadini et al. |
| 6,288,218 | B1 | 9/2001 | Levinson |
| 6,323,334 | B1 | 11/2001 | Kingsbury et al. |
| 6,905,827 | B2 | 6/2005 | Wohlgemuth et al. |
| 7,087,396 | B2 | 8/2006 | Tominaga et al. |
| 7,432,060 | B2 | 10/2008 | Lee |
| 2003/0228570 | A1 | 12/2003 | Yat Wah Tom et al. |
| 2004/0133079 | A1 | 7/2004 | Mazar et al. |
| 2005/0203046 | A1 | 9/2005 | Schmitz et al. |
| 2005/0250156 | A1 | 11/2005 | Shelovski |
| 2005/0272054 | A1 | 12/2005 | Cargill et al. |
| 2006/0216755 | A1 | 9/2006 | Lee |
| 2007/0042978 | A1 | 2/2007 | Girard et al. |
| 2007/0248981 | A1 | 10/2007 | Snider et al. |
| 2008/0003199 | A1 | 1/2008 | Lee |
| 2009/0192078 | A1 | 7/2009 | Lee |

FOREIGN PATENT DOCUMENTS

| | | |
|---|---|---|
| EP | 1731910 | 12/2006 |
| WO | 00/35473 | 6/2000 |
| WO | WO 00/35951 | 6/2000 |
| WO | 02/38794 | 5/2002 |
| WO | 03/094856 | 11/2003 |
| WO | 2004/056868 | 7/2004 |
| WO | 2007/127749 | 11/2007 |

OTHER PUBLICATIONS

Auer et al, "C-reactive protein and coronary artery disease," Jpn Heart J., 43(6):607-619 (2002).
Aukrust et al., "Cytokine network in congestive heart failure secondary to ischemic or idiopathic dilated cardiomyopathy," Am J Cardiol., 83(3):376-382 (1999).
Baumgarten et al., "Cytokines as emerging targets in the treatment of heart failure," Trends Cardiovasc Med., 10(5):216-223 (2000).
Bayés-Genís Antoni, "[The circulating NTproBNP level, a new biomarker for the diagnosis of heart failure in patients with acute shortness of breath]," Revista Española de Cardiologia, 58(10):1142-1144 (2005).
Blum et al., "Pathophysiological role of cytokines in congestive heart failure," Annu. Rev. Med., 52:15-27 (2001) (abstract).
Boisot et al., "Serial Sampling of ST2 Predicts 90-Day Mortality Following Destabilized Heart Failure," Journal of Cardiac Failure, 14:732-738 (2008).
Brint et al., "ST2 is an inhibitor of interleukin 1 receptor and Toll-like receptor 4 signaling and maintains endotoxin tolerance," Nat. Immunol., 5(4):373-379 (2004).
Bruneau, "Selective changes in natriuretic peptide and early response gene expression in isolated rat atria following stimulation by stretch or endothelin-1," Cardiovasc. Res., 28(10):1519-1525 (1994).
Brunner et al., "Increased levels of soluble ST2 protein and IgG1 production in patients with sepsis and trauma," Intensive Care Med., 30(7):1468-1473 (2004).
Carter et al., "Regulation of ST2L expression of T helper (Th) type 2 cells," Eur. J. Immunol , 31(10):2979-2985 (2001). (Abstract Only).
Chan et al., "Human IL-18 receptor and ST2L are stable and selective markers for the respective type 1 and type 2 circulating lymphocytes," J Immunol , 167(3):1238-1244 (2001). (Abstract).
Feldman et al., "C-reactive protein is an independent predictor of mortality in women with HIV-1 infection," J. Acquir. Immune Defic. Syndr., 32(2):210-214 (2003). (Abstract).
Forssmann et al., "The heart is the center of a new endocrine, paracrine, and neuroendocrine system," Arch. Histol. Cytol., 52 Suppl:293-315 (1989). (Abstract).
Frangogiannis et al., "Resident cardiac mast cells degranulate and release preformed TNF-alpha, initiating the cytokine cascade in experimental canine myocardial ischemia/reperfusion," Circulation., 98(7):699-710 (1998).
Galvani et al., "Prognostic influence of elevated values of cardiac troponin I in patients with unstable angina," Circulation, 95(8):2053-2059 (1997). (Abstract).
Gegenhuber et al., "B-type natriuretic peptide and amino terminal proBNP predict one-year mortality in short of breath patients independently of the baseline diagnosis of acute destabilized heart failure," Clinica Chimica Acta, 370(1-2):174-179 (2006). Goetze et al., "B-type natriuretic peptide and its precursor in cardiac venous blood from failing hearts," European Journal of Heart Failure, 7(1):69-74 (2005).
Gwechenberger et al., Cardiac myocytes produce interleukin-6 in culture and in viable border zone of reperfused infarctions. Circulation. Feb. 2, 1999;99(4):546-51.
Heeschen et al., Predictive value of C-reactive protein and troponin T in patients with unstable angina: a comparative analysis. CAPTURE Investigators. Chimeric c7E3 AntiPlatelet Therapy in Unstable angina Refractory to standard treatment trial. J Am Coll Cardiol. May 2000;35(6):1535-42. Abstract Only.
Januzzi et al., "Measurement of the Interleukin Family Member ST2 in Patients with Acute Dyspnea: Results from the PRIDE (Pro-Brain Natriuretic Peptide Investigation of Dyspnea in the Emergency Department) Study," J. Am. Coll. Cardiol., 50:607-613 (2007).

(Continued)

*Primary Examiner* — Carolyn L. Smith
(74) *Attorney, Agent, or Firm* — Fish & Richardson P.C.

(57) ABSTRACT

Measurement of circulating ST2 and natriuretic peptide (e.g., NT-proBNP) concentrations is useful for the prognostic evaluation of subjects, in particular for the prediction of adverse clinical outcomes, e.g., mortality, transplantation, and heart failure.

18 Claims, 14 Drawing Sheets

OTHER PUBLICATIONS

Januzzi et al., "NT-proBNP testing for diagnosis and short-term prognosis in acute destabilized heart failure: an international pooled analysis of 1256 patients: the International Collaborative of NT-proBNP Study," Eur. Heart J., 27(3):330-337 (2006).

Januzzi et al., "The N-terminal Pro-BNP investigation of dyspnea in the emergency department (PRIDE) study," Am. J. Cardiol., 95(8):948-954 (2005).

Januzzi et al., "The value of soluble ST2 measurement for the diagnostic and prognostic evaluation of patients with acute dyspnea," Circulation, 114(18):721 (2006) (abstract).

Januzzi et al., "Utility of amino-terminal pro-brain natriuretic Peptide testing for prediction of 1-year mortality in patients with dyspnea treated in the emergency department," Arch. Intern. Med., 166(3):315-320 (2006).

Kakkar et al., "The IL-33/ST2 pathway: Therapeutic target and novel biomarker," Nature Reviews Drug Discovery, 7(10):827-840 (2008).

Kida et al., Pathophysiological role of natriuretic peptides. Rinsho Byori. Aug. 1989;37(8):875-82. Abstract Only.

Kieser et al., "Identification of the primary growth response gene, ST2/T1, as a gene whose expression is differentially regulated by different protein kinase C isozymes," FEBS Lett., 372(23):189-193 (1995).

Knudsen et al., "Predictors of elevated B-type natriuretic peptide concentrations in dyspneic patients without heart failure: an analysis from the breathing not properly multinational study," Ann. Emerg. Med., 45(6):573-580 (2005).

Krauser et al., "Effect of body mass index on natriuretic peptide levels in patients with acute congestive heart failure: a ProBNP Investigation of Dyspnea in the Emergency Department (PRIDE) substudy," Am. Heart J., 149(4):744-750 (2005).

Kumar et al., Expression of ST2, an interleukin-1 receptor homologue, is induced by proinflammatory stimuli. Biochem Biophys Res Commun. Jun. 27, 1997;235(3):474-8.

Kuroiwa et al., "Construction of ELISA system to quantify human ST2 protein in sera of patients. Hybridoma," 19(2):151-159 (2000).

Kuroiwa K, et al., Identification of Human ST2 Protein in the Sera of Patients with Autoimmune Diseases. Biochemical and Biophysical Research Communications 2001; 284:1104-8.

Lee et al., "Novel markers for heart failure diagnosis and prognosis," Curr Opin Cardiol, 20(3):201-210 (2005).

Leyva et al., European Heart J., 19:1814-1822 (1998).

Lohning et al., "T1/ST2 is preferentially expressed on murine Th2 cells, independent of interleukin 4, interleukin 5, and interleukin 10, and important for Th2 effector function," Proc. Natl. Acad. Sci. U.S.A., 95(12):6930-6935 (1998).

MacGowan et al., Circulating interleukin-6 in severe heart failure. Am J Cardiol. Apr. 15, 1997;79(8):1128-31.

MacKenna et al., Role of mechanical factors in modulating cardiac fibroblast function and extracellular matrix synthesis. Cardiovasc Res. May 2000;46(2):257-63.

Maisel et al., "Bedside B-Type Natriuretic Peptide in the Emergency Diagnosis of Heart Failure With Reduced or Preserved Ejection Fraction," J. Am. Coll. Cardiol., 41:2010-7i (2003).

Maisel et al., "Primary results of the Rapid Emergency Department Heart Failure Outpatient Trial (REDHOT). A multicenter study of B-type natriuretic peptide levels, emergency department decision making, and outcomes in patients presenting with shortness of breath," J. Am. Coll. Cardiol., 44(6):1328-1333 (2004).

Maisel et al., "Rapid measurement of B-type natriuretic peptide in the emergency diagnosis of heart failure," N. Engl. J. Med., 347(3):161-167 (2002).

Mann et al., Stress activated cytokines and the heart. Cytokine Growth Factor Rev. Dec. 1996;7(4):341-54.

McCord et al., "Relationship between obesity and B-type natriuretic peptide levels," Arch. Intern. Med., 164(20):2247-2252 (2004).

Millenium Pharmaceuticals, Inc. Millenium Pharmaceuticals Identifies a Key mediator of Allergic Immune Response. Press Release Oct. 4, 1999, 2 pages.

Mitcham et al., T1/ST2 signaling establishes it as a member of an expanding interleukin-1 receptor family. J Biol Chem. Mar. 8, 1996;271(10):5777-83.

Moe et al., "Neurohormonal activation in severe heart failure: relations to patient death and the effect of treatment with flosequinan," Am. Heart. J., 139:587-95 (2000).

Mueller et al., "Increased Plasma Concentrations of Soluble ST2 are Predictive for 1-Year Mortality in Patients with Acute Destabilized Heart Failure," Clinical Chemistry, 54:752-756 (2008).

Mueller et al., "Use of B-type natriuretic peptide in the evaluation and management of acute dyspnea," New England Journal of Medicine, 350(7):647-654 (2004).

Mukoyama et al., Augmented secretion of brain natriuretic peptide in acute myocardial infarction. Biochem Biophys Res Commun. Oct. 15, 1991;180(1):431-6. Abstract Only.

Murphy et al., Signaling and transcription in T helper development. Annu Rev Immunol 2000;18:451-94.

Ng et al., Diagnosis of heart failure using urinary natriuretic peptides. Clin Sci (Lond). Feb. 2004;106(2):129-33.

Nozaki et al., Soluble Tumor Necrosis Factor Receptors are Elevated in Relation to Severity of Congestive Heart Failure, Jpn Circ J 1997; 61:657-64.

O'Neill et al., The IL-1 receptor/toll-like receptor superfamily: crucial receptors for inflammation and host defense. Immunol Today. May 2000;21(5):206-9.

Ohki R et al. Identification of mechanically induced genes in human monocytic cells by DNA microarrays. J. Hypertens., Apr. 2002; 20(4):685-691 Abstract Only.

Ohtsuka et al., Effect of beta-blockers on circulating levels of inflammatory and anti-inflammatory cytokines in patients with dilated cardiomyopathy. J Am Coll Cardiol. Feb. 2001;37(2):412-7.

Orús et al., Prognostic Value of Serum Cytokines in Patients with Congestive Heart Failure, J Heart Lung Transplant 2000; 19:419-25.

Oshikawa et al., "Acute eosinophilic pneumonia with increased soluble ST2 in serum and bronchoalveolar lavage fluid," Respir. Med., 95(6):532-533 (2001).

Oshikawa et al., "Elevated Soluble ST2 Protein Levels in Sera of Patients with Asthma with an Acute Exacerbation," Am. J. Respir. Crit. Care Med. 164:277-281 (2001).

Oshikawa et al., "Expression and function of the ST2 gene in a murine model of allergic airway inflammation," Clin. Exp. Allergy, 32(10):1520-1526 (2002).

Oshikawa et al., "Expression of ST2 in helper T lymphocytes of malignant pleural effusions," Am. J. Respir. Crit. Care Med., 165(7):1005-1009 (2002).

Oshikawa et al., "ST2 protein induced by inflammatory stimuli can modulate acute lung inflammation," Biochem. Biophys. Res. Commun., 299(1):18-24 (2002).

Pascual Figal Domingo et al., <<[Usefulness of NTproBNP in the emergency management of patients with severe syspnea and an uncertain heart failure diagnosis], Revista Española de Cardiología, 58(10):1155-1161 (2005).

Perrier et al., Am. J. Respir. Crit. Care Med., 156(2):492-496 (1997).

Potter et al., Mutations in the murine fitness 1 gene result in defective hematopoiesis. Blood. Sep. 1, 1997;90(5):1850-7.

Richards et al., "Plasma N-terminal pro-brain natriuretic peptide and adrenomedullin: new neurohormonal predictors of left ventricular function and prognosis after myocardial infarction," Circulation, 97:1921-1929 (1998).

Ridker et al., "Inflammation, Aspirin, and the Risk of Cardiovascular Disease in Apparently Healthy Men," New England J. Med., 336:973-979 (1997).

Rohde et al., "Circulating Cell Adhesion Molecules Are Correlated With Ultrasound-Based Assessment of Carotid Atherosclerosis," Arterial Sclerotic Vasc. Biol., 18:1765-1770 (1998).

Rohde et al., "Plasma Concentrations of Interleukin-6 and Abdominal Aortic Diameter Among Subjects Without Aortic Dilatation," Arterial Sclerotic Vasc. Biol., 19:1695-1699 (1999).

Roig et al., Serum interleukin-6 in congestive heart failure secondary to idiopathic dilated cardiomyopathy. Am J Cardiol. Sep. 1, 1998;82(5):688-90, A8.

Sabatine et al., "Multimarker approach to risk stratification in non-ST elevation acute coronary syndromes: simultaneous assessment of troponin I, C-reactive protein, and B-type natriuretic peptide," Circulation, 105(15):1760-1763 (2002).

Schmitz et al., "IL-33, an interleukin-1-like cytokine that signals via the IL-1 receptor-related protein ST2 and induces T helper type 2-associated cytokines," Immunity, 23(5):479-490 (2005).

Selvais et al., J Card Fail, Sep. 2000; 6(3):201-7. (Abstract Only).

Shimpo et al., "Serum levels of the interleukin-1 receptor family member ST2 predict mortality and clinical outcome in acute myocardial infarction" Circulation, 109(18):2186-2190 (2004).

Silver et al., Cong. Heart Fail., 10(5 suppl. 3) :1-30 (2004).

Strunk et al., "Impact of the history of congestive heart failure on the utility of B-type natriuretic peptide in the emergency diagnosis of heart failure: results from the Breathing Not Properly Multinational Study," Am. J. Med., 119(1):69 e1-11 (2006).

Sussman et al., Dance band on the Titanic: biomechanical signaling in cardiac hypertrophy. Circ Res. Nov. 15, 2002;91(10):888-98.

Sutton et al., Left ventricular remodeling after myocardial infarction: pathophysiology and therapy. Circulation. Jun. 27, 2000;101(25):2981-8.

Svensson et al., "Prognostic value of biochemical markers, 12-lead ECG and patient characteristics amongst patients calling for an ambulance due to a suspected acute coronary syndrome," Journal of Internal Medicine, 255(4):469-477 (2004).

Tajima et al., "The increase in serum soluble ST2 protein upon acute exacerbation of idiopathic pulmonary fibrosis," Chest, 124(4):1206-1214 (2003).

Tang Z, et al. Gene Expression profiling during the transition to failure in TNF-α over-expressing mice demonstrates the development of autoimmune myocarditis. Journal of Molecular and Cellular Cardiology 2004; 36:515-30.

Tominaga et al., [ST2 gene: a gene that is induced by growth stimulation and encoding a product highly similar to the interleukin 1 receptors] Seikagaku. May 1995;67(5):356-64. Review. Japanese.

Tominaga et al., "Nucleotide sequence of a complementary DNA for human ST2," Biochim. Biophys. Acta., 1171:215-218 (1992). (Abstract Only).

Tominaga et al., The existence of a growth-specific DNA binding factor for the promoter region of mouse ST2 gene. FEBS Lett. Nov. 14, 1994;354(3):311-4.

Tominaga, FEBS Lett., "A putative protein of a growth specific cDNA from BALB/c-3T3 cells is highly similar to the extracellular portion of mouse interleukin 1 receptor," FEBS Lett., 258:301-304 (1989).

Townsend et al., T1/ST2-deficient mice demonstrate the importance of T1/ST2 in developing primary T helper cell type 2 responses. J Exp Med. Mar. 20, 2000;191(6):1069-76.

Tsutamoto et al., Interleukin-6 spillover in the peripheral circulation increases with the severity of heart failure, and the high plasma level of interleukin-6 is an important prognostic predictor in patients with congestive heart failure. J Am Coll Cardiol. Feb. 1998;31(2):391-8.

Tung et al., "Utility of B-type natriuretic peptide for the evaluation of intensive care unit shock," Crit. Care Med., 32(8):1643-1647 (2004).

Van Kimmenade et al., Utility of amino-terminal pro-brain natriuretic peptide, galectin-3, and apelin for the evaluation of patients with acute heart failure. J Am Coll Cardiol. Sep. 19, 2006;48(6):1217-24.

Vidal et al., Prognostic Value of Cytokines and Neurohormones in Severe Heart Failure, Rev Esp Cardiol 2002; 55(5):481-6.

Wang et al., "Expression of Interleukin-1β, Interleukin-1 Receptor, and Interleukin-1 Receptor Antagonist mRNA in Rat Carotid Artery after Balloon Angioplasty," Biochem. Biophyl. Res. Comm., 271:138-143 (2000).

Weinberg et al., "Expression and regulation of ST2, an interleukin-1 receptor family member, in cardiomyocytes and myocardial infarction," Circulation, 106(23):2961-2966 (2002).

Weinberg et al., "Identification of serum soluble ST2 receptor as a novel heart failure biomarker," Circulation, 107(5):721-726 (2003).

Yamaoka et al., Anti-inflammatory cytokine profile in human heart failure: behavior of interleukin-10 in association with tumor necrosis factor-alpha. Jpn Circ J. Dec. 1999;63(12):951-6.

Zebrack et al., Usefulness of high-sensitivity C-reactive protein in predicting long-term risk of death or acute myocardial infarction in patients with unstable or stable angina pectoris or acute myocardial infarction. Am J Cardiol. Jan. 15, 2002;89(2):145-9.

International Preliminary Report on Patentability for PCT/US2009/040941, issued Oct. 19, 2010.

International Search Report for PCT/US2009/040941, completed Dec. 2, 2009, mailed Dec. 3, 2009.

Written Opinion of the International Searching Authority for PCT/US2009/040941, completed Dec. 2, 2009, mailed Dec. 3, 2009.

Kip et al., "The Problem With Composite End Points in Cardiovascular Studies," *J Am. Coll. Cardiol.* 51(7):701-707, 2008.

Ordonez-Llanos et al., "A Formula Combining ST2 and NT-proBNP Enhances Prognostic Accuracy in Patients with Heart Failure," *Clin. Chem.*, American Association for Clinical Chemistry, Washington, D.C. 54(6):A99 (2008).

Supplementary European Search Report and Search Opinion for European Application No. EP 09731842, search and opinion mailed Apr. 1, 2011, search completed Feb. 28, 2011.

| Area under the ROC curve (AUC) | 0.800 |
|---|---|
| Standard error | 0.0637 |
| 95% Confidence interval | 0.659 to 0.901 |
| Significance level P (Area=0.5) | 0.0001 |

Criterion values and coordinates of the ROC curve

| Criterion | Sensitivity | 95% CI | Specificity | 95% CI | +LR | -LR |
|---|---|---|---|---|---|---|
| >=2 | 100.00 | 86.7 - 100.0 | 0.00 | 0.0 - 15.6 | 1.00 | |
| >2.5 | 100.00 | 86.7 - 100.0 | 13.64 | 3.1 - 34.9 | 1.16 | 0.00 |
| >2.6 | 96.15 | 80.3 - 99.4 | 18.18 | 5.3 - 40.3 | 1.18 | 0.21 |
| >2.8 | 96.15 | 80.3 - 99.4 | 27.27 | 10.8 - 50.2 | 1.32 | 0.14 |
| >2.9 | 92.31 | 74.8 - 98.8 | 31.82 | 13.9 - 54.9 | 1.35 | 0.24 |
| >3 | 92.31 | 74.8 - 98.8 | 50.00 | 28.2 - 71.8 | 1.85 | 0.15 |
| >3.1 | 88.46 | 69.8 - 97.4 | 63.64 | 40.7 - 82.8 | 2.43 | 0.18 |
| >3.2 | 84.62 | 65.1 - 95.5 | 68.18 | 45.1 - 86.1 | 2.66 | 0.23 |
| >3.3 * | 80.77 | 60.6 - 93.4 | 72.73 | 49.8 - 89.2 | 2.96 | 0.26 |
| >3.6 | 53.85 | 33.4 - 73.4 | 72.73 | 49.8 - 89.2 | 1.97 | 0.63 |
| >3.7 | 50.00 | 29.9 - 70.1 | 77.27 | 54.6 - 92.1 | 2.20 | 0.65 |
| >3.9 | 50.00 | 29.9 - 70.1 | 81.82 | 59.7 - 94.7 | 2.75 | 0.61 |
| >4 | 46.15 | 26.6 - 66.6 | 81.82 | 59.7 - 94.7 | 2.54 | 0.66 |
| >4.1 | 42.31 | 23.4 - 63.1 | 90.91 | 70.8 - 98.6 | 4.65 | 0.63 |

MACERS

| Area under the ROC curve (AUC) | 0.766 |
|---|---|
| Standard error | 0.0734 |
| 95% Confidence interval | 0.621 to 0.876 |
| Significance level P (Area=0.5) | 0.0003 |

Criterion values and coordinates of the ROC curve

| | | | | | | |
|---|---|---|---|---|---|---|
| >3.1 | 89.47 | 66.8 - 98.4 | 51.72 | 32.5 - 70.5 | 1.85 | 0.20 |
| >3.2 | 84.21 | 60.4 - 96.4 | 55.17 | 35.7 - 73.5 | 1.88 | 0.29 |
| >3.3 | 84.21 | 60.4 - 96.4 | 62.07 | 42.3 - 79.3 | 2.22 | 0.25 |
| >3.4 | 78.95 | 54.4 - 93.8 | 62.07 | 42.3 - 79.3 | 2.08 | 0.34 |
| >3.5 * | 78.95 | 54.4 - 93.8 | 68.97 | 49.2 - 84.7 | 2.54 | 0.31 |
| >3.6 | 63.16 | 38.4 - 83.6 | 72.41 | 52.8 - 87.2 | 2.29 | 0.51 |
| >3.7 | 57.89 | 33.5 - 79.7 | 75.86 | 56.5 - 89.7 | 2.40 | 0.56 |
| >3.9 | 57.89 | 33.5 - 79.7 | 79.31 | 60.3 - 92.0 | 2.80 | 0.53 |
| >4 | 52.63 | 28.9 - 75.5 | 79.31 | 60.3 - 92.0 | 2.54 | 0.60 |

PREDICTING RISK OF MAJOR ADVERSE CARDIAC EVENTS

CLAIM OF PRIORITY

This application claims the benefit of U.S. Provisional Patent Application Ser. No. 61/046,158, filed on Apr. 18, 2008, the entire contents of which are hereby incorporated by reference.

TECHNICAL FIELD

The invention relates to methods for predicting risk of major adverse cardiac events and detecting the presence of severe disease based on circulating levels of ST2 and natriuretic peptides (NP), e.g., NT-proBNP, alone or in combination with other biomarkers.

BACKGROUND

Clinical evaluation for determination of disease severity and risk of major adverse cardiac events (MACE), e.g., mortality due to heart failure, may not always be apparent. The decision whether to treat a subject aggressively or conservatively, or to admit the subject as an inpatient or to send them home, may sometimes be made solely on a physician's clinical assessment or "gut feeling" as to the individual's actual condition. A formula for determining a subject's likelihood of an adverse outcome, e.g., mortality, transplantation, and/or readmission, would significantly enhance the physician's ability to make informed treatment decisions, improve patient care and reduce overall healthcare costs.

SUMMARY

The present invention is based, at least in part, on the use of changes in serum levels of the biomarker ST2 (Growth Stimulation-Expressed Gene 2, also known as Interleukin 1 Receptor Like 1 (IL1RL-1)), in combination with levels of a natriuretic peptide (NP) such as the inactive N-terminal fragment of brain-type natriuretic peptide (NT-pro-BNP), to predict the likelihood of a major adverse cardiac event (MACE), e.g., recurrence of the initial cardiac event (e.g., a second MI); angina; decompensation of heart failure; admission for cardiovascular disease (CVD); mortality due to CVD; or transplant, within a specific time period, e.g., 30 days, 3 or 6 months, or a year or more, or to detect the presence of severe disease (e.g., severe disease likely to require transplantation or other aggressive treatment). These methods can be used to predict clinical outcome, e.g., in patients hospitalized after an acute cardiac event.

In some embodiments, the methods described herein include monitoring changes in ST2 levels over time (e.g., an ST2 ratio) and determining an NP level, to provide diagnostic and prognostic evaluation of patients, e.g., patients with non-specific symptoms, e.g., acutely dyspneic patients and those with chest pain, or patients who have been diagnosed with heart failure. NPs include the forms of the brain natriuretic peptides, i.e., NT-proBNP, proBNP, and BNP, and the atrial natriuretic peptides, i.e., NT-proANP, proANP, and ANP. In preferred embodiments, the NP is NT-proBNP.

In some embodiments, the invention features methods for evaluating the risk of a MACE within a specific time period, e.g., 30, 60, 90, or 180 days (e.g., one, two, three, or six months), or one, two, or five years, for a subject. The methods can include determining ratios of ST2 and a level of an NP, e.g., NT-proBNP, and using those ratios and levels to determine risk of MACE, as described herein. Determining a ratio of ST2 can include obtaining at least two samples, e.g., samples of blood, serum, plasma, urine, or body tissue from the subject (both samples are from the same fluid or tissue, taken at two different time points); determining levels of ST2 in the samples; and dividing the biomarker levels of ST2 in the earlier samples into the levels of ST2 in the later sample, thereby arriving at a ratio of ST2. Such a ratio provides an indication of how the levels of ST2 are changing in the subject over time. Thus, in some embodiments, the methods include determining or obtaining a first ST2 level, e.g., a baseline level in a sample taken, e.g., at admission or at initiation of treatment, and a second ST2 level, e.g., in a sample taken some time later, e.g., one, two, three, four, or more days later. In addition, the methods will generally include determining or obtaining an NP level, e.g., an NT-proBNP level at least at the second time point, e.g., in a sample of blood, serum, plasma, urine, or body tissue from the subject.

In one aspect, the invention provides methods, e.g., computer-implemented methods, for evaluating the risk of a major adverse cardiac event (MACE) for a subject within one year. The methods include determining a MACE risk score (MACERS) for a subject based upon, at least in part, the ratio of a second level of Growth Stimulation-Expressed Gene 2 (ST2) in the subject at a second time (ST2 T0) to a first level of ST2 in the subject at a first time (ST2 T1), in combination with a weighted logarithm of a level of a natriuretic peptide (NP) in the subject at the second time (NP T1), and comparing the MACERS to a reference MACERS; wherein the MACERS in comparison with the reference MACERS indicates the subject's risk of a MACE within one year.

In some embodiments, the methods described herein include the use of the following formula to determine a subject's risk of a MACE:

$$X = (ST2T1/ST2T0) + \alpha \ln(NPT1)$$

In preferred embodiments, the ST2 ratios and NT-proBNP levels, are used to determine a MACE risk score using the following formula:

$$X = (ST2T1/ST2T0) + \alpha \ln(NTproBNPT1)$$

In some embodiments, the coefficient alpha is 0.33.

In some embodiments, the subject's MACE risk score is compared to a reference MACE risk score (e.g., a threshold value). A comparison of the subject's MACE risk score versus the reference score indicates the subject's risk of a MACE within the specific time period. In some embodiments, the specific time period is one year.

In some embodiments, the reference MACE risk score represents the score in a subject or group of subjects who have a low risk of death within one year. In some embodiments, a subject MACE risk score that is greater than or equal to the reference MACE risk score indicates that the subject has an elevated, i.e., statistically significantly elevated, risk of death within one year. In some embodiments, the elevated risk of death is at least 20% higher, e.g., 30%, 40%, or 50% higher.

In some embodiments, the methods include determining a MACE risk score, and optionally selecting or modifying a treatment for the subject, based on the MACE risk score. For example, if the MACE risk score is more than a selected reference, then the subject has a high risk and should be treated more aggressively; if the subject is already being treated, then the subject is not responding favorably to the current treatment and a new treatment should be selected, i.e., an alternate treatment to which the patient may respond more favorably.

In some embodiments, the subject exhibits one or more non-specific symptoms, e.g., chest pain or discomfort, shortness of breath (dyspnea), nausea, vomiting, eructation, sweating, palpitations, lightheadedness, fatigue, and fainting. In some embodiments, the symptom is dyspnea or chest pain.

In some embodiments, the subject does not have a cardiovascular disorder. In various embodiments, the subject has a pulmonary disorder, e.g., acute infection (e.g., pneumonia), chronic obstructive pulmonary disease (COPD), and pulmonary embolism.

In certain embodiments, the subject has a liver disorder, e.g., a liver disorder associated with chemotherapy, alcohol toxicity, or drug toxicity as determined by standard liver function laboratory tests.

In some embodiments, the methods further include determining the level of an adjunct (non-ST2, non-IL-33, non-NT-proBNP) biomarker, e.g., Troponin, CRP, D-dimers, BUN, albumin, liver function enzymes, measures of renal function, e.g., creatinine, creatinine clearance rate, or glomerular filtration rate, and/or bacterial endotoxin, in the sample; and comparing the level of the adjunct biomarker in the sample to a reference level of the adjunct biomarker. The level of the adjunct biomarker in the sample as compared to the reference, in combination with the MACE risk score in the sample as compared to a reference MACE risk score, indicates whether the subject has an elevated risk of death within a specific time period, and/or has a present severe disease. In some embodiments, the methods include determining a change in levels over time (e.g., a ratio) for the adjunct biomarker, by comparing a first level, e.g., a baseline level, to a second level, e.g., a level taken some time later, e.g., one, two, three, four, or more days later.

In some embodiments, the subject has a BMI of 25-29, a BMI of $\geq 30$, or renal insufficiency, e.g., the subject is selected on the basis that they have a BMI of 25-29, a BMI of $\geq 30$, or renal insufficiency.

In another aspect, the invention includes methods for evaluating a subject's condition over time, e.g., for evaluating the efficacy of a treatment in a subject. The methods include determining a first MACE risk score in a subject, based upon a ratio of a first, baseline level of ST2 and a second level of ST2 taken at a second time point, and a first level of an NP, e.g., NT-proBNP, taken at the second time point, to determine a first MACE risk score; and determining a second MACE risk score based upon a ratio of the first, baseline level of ST2 and a third ST2 level taken at a third time point, and a level of an NP, e.g., NT-proBNP, taken at the third time point, wherein the third time point is some time after the second time point, e.g., days, weeks, months, or years later. A comparison of the first and second MACE risk scores indicates whether the subject is declining, improving, or maintaining the same status, e.g., indicates the efficacy of the treatment in the subject. For example, a second MACE risk score that is lower than the first MACE risk score indicates that the treatment is effective.

As used herein, a "sample" includes any bodily fluid or tissue, e.g., one or more of blood, serum, plasma, urine, and body tissue. In certain embodiments, a sample is a serum, plasma, or blood sample.

An antibody that "binds specifically to" an antigen, binds preferentially to the antigen in a sample containing other proteins.

The methods and kits described herein have a number of advantages. For example, the methods can be used to determine whether a patient should be admitted or held as an inpatient for further assessment, regardless of whether a definitive diagnosis has been made. For example, the methods can be used for risk stratification of a given subject, e.g., to make decisions regarding the level of aggressiveness of treatment that is appropriate for the subject, based on their MACE risk score as determined by a method described herein. Better treatment decisions can lead to reduced morbidity and mortality, and better allocation of scarce health care resources. The methods described herein can be used to make general assessments as to whether a patient should be further tested to determine a specific diagnosis. The methods described herein can also be used for patient population risk stratification, e.g., to provide information about clinical performance or expected response to a therapeutic intervention. The methods described herein can be used regardless of the underlying cause or ultimate diagnosis, and therefore are not limited to specific indications.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting.

All publications, patent applications, patents, sequences, database entries, and other references mentioned herein are incorporated by reference in their entirety. In addition, the present application incorporates by reference the entire contents of U.S. patent application Ser. No. 11/789,169, and international patent application nos. PCT/US2007/067626, PCT/US2007/067914, and PCT/US2007/068024.

In case of conflict, the present specification, including definitions, will control.

Other features and advantages of the invention will be apparent from the following detailed description and Figures, and from the claims.

DETAILED DESCRIPTION

Figure 1:
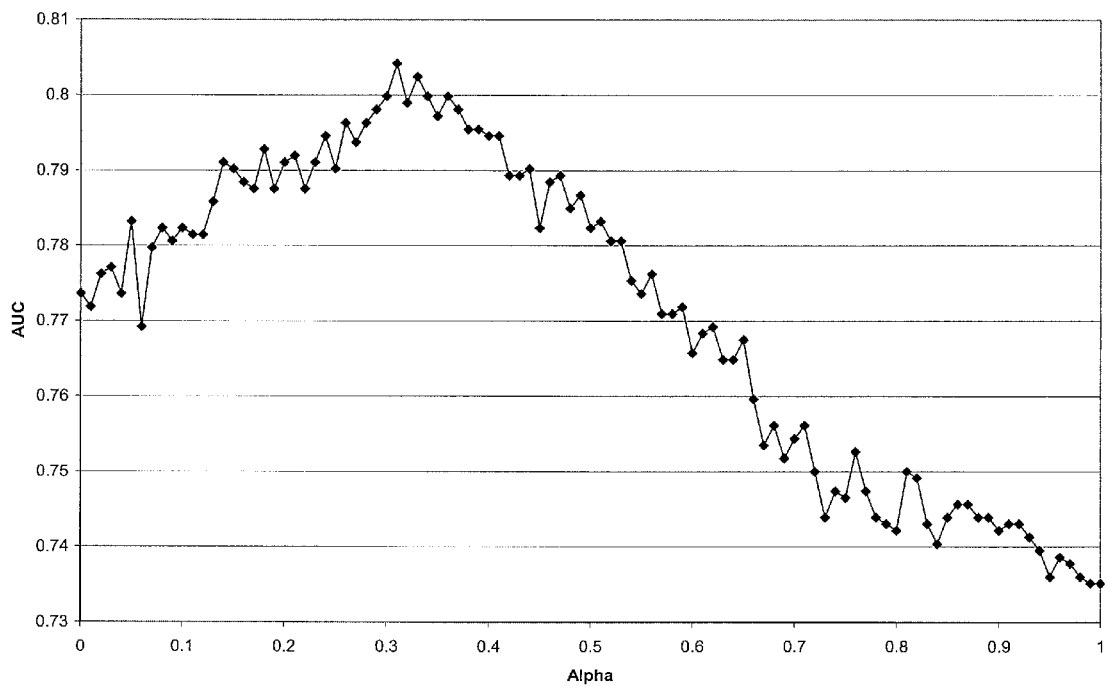
FIG. 1 is a line graph of Receiver Operating Characteristic (ROC) score analysis of the algorithm combining the ST2 ratio and the week 2 NT-proBNP value.

Clinical evaluation of patients, particularly patients with non-specific symptoms such as dyspnea or chest pain, is often challenging. The results described herein provide evidence that MACE risk scores based on ST2 and NT-proBNP are useful in the prognostic evaluation of patients, regardless of the underlying cause of their disease. The MACE risk score is a powerful indicator of severe disease and imminent death, as demonstrated herein in several different populations.

Predicting MACE

Elevated concentrations of ST2 are markedly prognostic for death within one year, with a dramatic divergence in survival curves for those with elevated ST2 soon after presentation, regardless of the underlying diagnosis. As one example, there is a dramatic relationship between elevations of ST2 and the risk for mortality within one year following presentation with dyspnea. The relationship between ST2 and death in dyspneic patients was independent of diagnosis, and superseded all other biomarker predictors of mortality in this setting, including other markers of inflammation, myonecrosis, renal dysfunction, and most notably NT-proBNP, a marker recently described as having value for predicting death in this population (Januzzi et al., Arch. Intern. Med. 166(3):315-20 (2006)). Indeed, most of the mortality in the study was concentrated among subjects with elevated ST2 levels at presentation; however, the combination of an elevated ST2 and NT-proBNP was associated with the highest rates of death within one year.

Such a multi-marker approach for risk stratification has been generally proposed for patients with acute coronary syndromes (Sabatine et al., Circulation 105(15):1760-3 (2002)), but no such strategy has yet been proposed for the evaluation for the patient with non-specific symptoms such as undifferentiated dyspnea or general complaint of chest pain.

Determining Severity of Disease

Elevated MACE risk scores are correlated with the presence of severe disease in a subject, regardless of the underlying cause of the disease. As one example, in a population of patients presenting with chest pain, the highest scores were associated with an increased risk of adverse events, including transplantation, which are generally associated with the presence of severe disease.

Therefore, for undiagnosed subjects, the methods described herein can be used to determine how aggressively a diagnosis should be sought; a high ST2 level would indicate the presence of severe disease, and suggest that the subject should be treated as a high-risk case. For subjects with a known diagnosis, the methods described herein can be used to help determine the severity of the underlying pathology; again, a higher ST2 level is associated with more severe disease.

General Methodology—Determining a Subject's MACE Risk Score

In general, the methods described herein include evaluating circulating levels (e.g., levels in blood, serum, plasma, urine, or body tissue) of ST2 and NT-proBNP in a subject, e.g., a mammal, e.g., a human. These levels provide information regarding the subject's likelihood of experiencing an adverse outcome, e.g., mortality, e.g., within a specific time period, e.g., 30 days, 60 days, 90 days, 6 months, one year, two years, three years, or five years. These levels also provide information regarding the severity of disease in the subject. In some embodiments, a level of ST2 is determined a first time (T0), e.g., at presentation, e.g., at 2, 4, 6, 8, 12, 18, and/or 24 hours, and/or 1-3 or 1-7 days, after the onset of symptoms. Then levels of ST2 and NT-proBNP are determined a second time (T1); the second time point can be, e.g., at least 1, 2, 4, 6, 8, 12, 18, or 24 hours, 1-7 days, 1-14 days, or 2-14 days, e.g., up to 14 days, after the first time point. These levels are used to determine a MACE risk score, using the following formula:

$$X = (ST2T1/ST2T0) + \alpha \ln(NTproBNPT1)$$

The coefficient alpha is a weighting factor for the variable it acts on. In some embodiments, the coefficient alpha is between 0.25 and 0.5, e.g., about 3, e.g., 0.33.

Evaluating circulating levels of ST2 and NTpro-BNP in a subject typically includes obtaining a biological sample, e.g., serum, plasma or blood, from the subject. Levels of ST2 and NTpro-BNP in the sample can be determined by measuring levels of polypeptide in the sample, using methods known in the art and/or described herein, e.g., immunoassays such as enzyme-linked immunosorbent assays (ELISA). For example, in some embodiments a monoclonal antibody is contacted with the sample; binding of the antibody is then detected and optionally quantified, and levels of the protein are determined based on levels of antibody binding. Alternatively, levels of ST2 and NTpro-BNP mRNA can be measured, again using methods known in the art and/or described herein, e.g., by quantitative PCR or Northern blotting analysis.

In some embodiments, the MACE risk score is calculated using a computing device, e.g., a personal computer.

Once a MACE risk score has been determined, the MACE risk score can be compared to a reference score. In some embodiments, the reference score will represent a threshold level, above which the subject has an increased risk of death, and/or has a severe disease. The reference score chosen may depend on the methodology used to measure the levels of ST2. For example, in some embodiments, where circulating levels of soluble ST2 are determined using an immunoassay, e.g., as described herein, the reference score is about 3, e.g., 3.2 or 3.5, and a score above that reference level indicates that the subject has an increased risk of death, and/or has a severe disease.

Where more than one MACE risk score has been determined as described herein, a change in the score indicates whether the subject has an increased or decreased risk of death. A score that increases means that the subject has an increasing risk of imminent death, e.g., an increasingly poor prognosis, and that a treatment is not working or should be changed or initiated. Scores that decrease over time indicate that the subject has a decreasing risk of imminent death, e.g., an increasingly positive prognosis, and can be indicative of the efficacy of a treatment, for example, and the treatment should be continued, or, if the score becomes low enough, possibly discontinued. As one example, increasing scores may indicate a need for more aggressive treatment or hospitalization (e.g., initial admission or hospitalization in a more acute setting, e.g., in an intensive care unit, or the use of telemetry or other methods for monitoring the subject's cardiac status), while decreasing scores may indicate the possibility of less aggressive treatment, a short hospitalization, or discharge. This information allows a treating physician to make more accurate treatment decisions; for example, the subject may be admitted to the hospital as an inpatient, e.g., in an acute or critical care department Additional testing can be performed, e.g., to determine the subject's actual condition. More aggressive treatment may be administered either before or after additional testing. For example, in the case of a suspected myocardial infarction (MI), the subject may be sent for more extensive imaging studies and/or cardiac catheterization.

In some embodiments, the methods include the use of additional diagnostic methods to identify underlying pathology. Any diagnostic methods known in the art can be used, and one of skill in the art will be able to select diagnostic methods that are appropriate for the subject's symptoms. In some embodiments, the methods described herein include other diagnostic methods in addition to or as an alternative to the measurement of other biomarkers, e.g., physical measurements of lung function or cardiac function as are known in the art.

For example, the methods described herein include determining a MACE risk score along with measuring one or more additional biomarkers that aid in the subject's diagnosis. As one example, for a subject who has chest pain or dyspnea, biomarkers indicative of cardiac disease can be measured, e.g., cardiac troponin (cTn), e.g., cTnI, BNP, and/or ANP; alternatively or in addition, biomarkers of pulmonary disease can be measured, e.g., D-dimers for pulmonary embolism. Thus, in subjects presenting with symptoms that include MI in their differential diagnoses, the methods can include measuring levels of, e.g., cTnI, BNP, or proBNP in addition to determining a MACE risk score, to determine whether the subject is having an MI. In subjects presenting with symptoms that include heart failure (HF) in their differential diagnoses, the methods can include measuring levels of BNP or proBNP in addition to determining a MACE risk score, to determine whether the subject is having HF. In subjects presenting with symptoms that include COPD in their differential diagnoses, the methods can include measuring lung function in addition to determining a MACE risk score, to determine whether the subject has COPD. One of skill in the art will appreciate that there are a number of additional diagnostic methods that can be applied, depending on the situation and the subject's condition. In some embodiments, the methods include measuring levels of BUN, and the presence of elevated BUN and elevated determining a MACE risk score places the subject in the highest risk category.

ST2

The ST2 gene is a member of the interleukin-1 receptor family, whose protein product exists both as a trans-membrane form, as well as a soluble receptor that is detectable in serum (Kieser et al., FEBS Lett. 372 (2-3):189-93 (1995); Kumar et al., J. Biol. Chem. 270(46):27905-13 (1995); Yanagisawa et al., FEBS Lett. 302(1):51-3 (1992); Kuroiwa et al., Hybridoma 19(2):151-9 (2000)). ST2 was recently described to be markedly up-regulated in an experimental model of heart failure (Weinberg et al., Circulation 106(23): 2961-6 (2002)), and preliminary results suggest that ST2 concentrations may be elevated in those with chronic severe HF (Weinberg et al., Circulation 107(5):721-6 (2003)) as well as in those with acute myocardial infarction (MI) (Shimpo et al., Circulation 109(18):2186-90 (2004)).

The trans-membrane form of ST2 is thought to play a role in modulating responses of T helper type 2 cells (Lohning et al., Proc. Natl. Acad. Sci. U.S.A. 95(12):6930-5 (1998); Schmitz et al., Immunity 23(5):479-90 (2005)), and may play a role in development of tolerance in states of severe or chronic inflammation (Brint et al., Nat. Immunol. 5(4):373-9 (2004)), while the soluble form of ST2 is up-regulated in growth stimulated fibroblasts (Yanagisawa et al., 1992, supra). Experimental data suggest that the ST2 gene is markedly up-regulated in states of myocyte stretch (Weinberg et al., 2002, supra) in a manner analogous to the induction of the BNP gene (Bruneau et al., Cardiovasc. Res. 28(10):1519-25 (1994)).

Tominaga, FEBS Lett. 258:301-304 (1989), isolated murine genes that were specifically expressed by growth stimulation in BALB/c-3T3 cells; they termed one of these genes St2 (for Growth Stimulation-Expressed Gene 2). The St2 gene encodes two protein products: ST2, which is a soluble secreted form; and ST2L, a transmembrane receptor form that is very similar to the interleukin-1 receptors. The HUGO Nomenclature Committee designated the human homolog, the cloning of which was described in Tominaga et al., Biochim. Biophys. Acta. 1171:215-218 (1992), as Interleukin 1 Receptor-Like 1 (IL1RL1). The two terms are used interchangeably herein.

The mRNA sequence of the shorter, soluble isoform of human ST2 can be found at GenBank Acc. No. NM_003856.2, and the polypeptide sequence is at GenBank Acc. No. NP_003847.2; the mRNA sequence for the longer form of human ST2 is at GenBank Acc. No. NM_016232.4; the polypeptide sequence is at GenBank Acc. No. NP_057316.3. Additional information is available in the public databases at GeneID: 9173, MIM ID #601203, and UniGene No. Hs.66. In general, in the methods described herein, the soluble form of ST2 polypeptide is measured.

Methods for detecting and measuring ST2 are known in the art, e.g., as described in U.S. Pat. Pub. Nos. 2003/0124624, 2004/0048286 and 2005/0130136, the entire contents of which are incorporated herein by reference. Kits for measuring ST2 polypeptide are also commercially available, e.g., the ST2 ELISA Kit manufactured by Medical & Biological Laboratories Co., Ltd. (MBL International Corp., Woburn, Mass.), no. 7638. In addition, devices for measuring ST2 and other biomarkers are described in U.S. Pat. Pub. No. 2005/0250156.

Natriuretic Peptides

Natriuretic peptides are a family of vasoactive peptide hormones that act as balanced arterial and venous vasodilators, regulating natriuresis and diuresis. Circulating levels of these hormones are under investigation for use in enhancing diagnostic and prognostic assessment of patients with cardiovascular disease. Previous studies have demonstrated that circulating levels of NT-proBNP are increased in patients with acute MI and predict mortality (Talwar et al., Eur. Heart J. 21:1514-1521 (2000); Omland et al., Am. J. Cardiol. 76:230-235 (1995) Sabatine et al., J. Am. Coll. Cardiol. 44:1988-1995 (2004), demonstrated a link between the severity of an acute ischemic insult and the circulating levels of BNP. Methods for measuring NT-proBNP are known in the art, see, e.g., Talwar et al., 2000, supra; Omland et al., 1995, supra; Sabatine et al., 2004, supra; Alehagen and Dahlström, "Can NT-proBNP predict risk of cardiovascular mortality within 10 years? Results from an epidemiological study of elderly patients with symptoms of heart failure," Int J. Cardiol. 2008 Apr. 11 [Epub ahead of print]; and Kavsak et al., Clin Chem. 54(4):747-51 (2008).

It is believed that, while the examples presented herein relate to NT-proBNP, any of the NPs can be used in the methods described herein. In some embodiments, more than one NP can be measured.

Other Biomarkers

The methods described herein can also include measuring levels of other biomarkers in addition to ST2 and an NP. Suitable biomarkers include troponin, CRP, IL-6, D-dimers, BUN, liver function enzymes, albumin, measures of renal function, e.g., creatinine, creatinine clearance rate, or glomerular filtration rate, and/or bacterial endotoxin. Methods for measuring these biomarkers are known in the art, see, e.g., U.S. Pat. Pub. Nos. 2004/0048286 and 2005/0130136 to Lee et al.; Dhalla et al., Mol. Cell. Biochem. 87:85-92 (1989); Moe et al., Am. Heart. J. 139:587-95 (2000); Januzzi et al., Eur. Heart J. 27(3):330-7 (2006); Maisel et al., J. Am. Coll. Cardiol. 44(6):1328-33 (2004); and Maisel et al., N. Engl. J. Med. 347(3):161-7 (2002), the entire contents of which are incorporated herein by reference. Liver function enzymes include alanine transaminase (ALT); aspartate transaminase (AST); alkaline phosphatase (ALP); and total bilirubin (TBIL).

In these embodiments, a MACE risk score and levels of one or more additional biomarkers are determined, and the information from the score and a comparison of the biomarkers with their respective reference levels provides additional information regarding the subject's risk of death and/or the presence of a severe disease in the subject, which may provide more accurate and specific information regarding the subject's risk. The levels can then be compared to a reference ratio that represents a threshold ratio above which the subject has an increased risk of death, and/or has a severe disease.

Selecting a Treatment—Aggressive vs. Conservative

Once it has been determined that a subject has a MACE risk score above a predetermined reference score, the information can be used in a variety of ways. For example, if the subject has an elevated score, e.g., as compared to a reference level, a decision to treat aggressively can be made, and the subject can be, e.g., admitted to a hospital for treatment as an inpatient, e.g., in an acute or critical care department. Portable test kits could allow emergency medical personnel to evaluate a subject in the field, to determine whether they should be transported to the ED. Triage decisions, e.g., in an ED or other clinical setting, can also be made based on information provided by a method described herein. Those patients with high scores can be prioritized over those with lower scores.

The methods described herein also provide information regarding whether a subject is improving, e.g., responding to a treatment, e.g., whether a hospitalized subject has improved sufficiently to be discharged and followed on an outpatient basis. In general, these methods will include d determining a MACE risk score for the subject multiple times. A decrease in MACE risk score over time indicates that the subject is likely to be improving. The most recent MACE risk score can also be compared to a reference score, as described herein, to determine whether the subject has improved sufficiently to be discharged.

The subject may also be considered for inclusion in a clinical trial, e.g., of a treatment that carries a relatively high risk. The subject can be treated with a regimen that carries a relatively higher risk than would be considered appropriate for someone who had a lower risk of imminent MACE, e.g., a MACE within 30 days or within 1 year of presentation.

Beyond the clinical setting, information regarding a subject's MACE risk score can be used in other ways, e.g., for payment decisions by third party payors, or for setting medical or life insurance premiums by insurance providers. For example, a high MACE risk score, e.g., a score above a predetermined threshold score, may be used to decide to increase insurance premiums for the subject.

Patient Populations

The methods described herein are useful in a wide variety of clinical contexts. For example, the methods can be used for general population screening, including screening by doctors, e.g., in hospitals and outpatient clinics, as well as the ED. As one example, a MACE risk score can be determined at any time, and if the MACE risk score is elevated, the physician can act appropriately.

Although the methods described herein can be used for any subject, at any time, they are particularly useful for those subjects for whom a diagnosis, or the severity of a condition, is difficult to determine. For example, such subjects may present with non-specific symptoms, e.g., symptoms that do not indicate a specific diagnosis. Non-specific symptoms include, but are not limited to, chest pain or discomfort, shortness of breath, nausea, vomiting, eructation, sweating, palpitations, lightheadedness, fatigue, and fainting. Each symptom can have varied etiology.

Chest Pain

Chest pain is the chief complaint in about 1 to 2 percent of outpatient visits, and although the cause is often noncardiac, heart disease remains the leading cause of death in the United States. Therefore, distinguishing between serious and benign causes of chest pain is crucial. The methods described herein are useful in making this determination.

A subject presenting to the ED with chest pain may have esophageal pain, an ulcer, acute lung problems such as pulmonary embolus (PE) (potentially fatal), rupturing or dissecting aneurysm (highly lethal), gall bladder attack, pericarditis (inflammation of the sack around the heart), angina pectoris (cardiac pain without damage), or an MI (potentially fatal). A precise diagnosis may be difficult to make immediately, but the decision whether to admit the subject or to treat them conservatively should generally be made immediately. If the methods described herein indicate that the subject has an increased risk of an adverse clinical outcome, e.g., imminent MACE or severe disease, then the decision can be made to treat the subject aggressively, to potentially prevent the adverse outcome.

Additional information about treatment and diagnosis of chest pain may be found, e.g., in Cayley, Am. Fam. Phys. 72(10):2012-2028 (2005).

Dyspnea

Dyspnea, or shortness of breath (also defined as abnormal or uncomfortable breathing), is a common symptom of subjects on presentation to the ED. The differential diagnosis for dyspnea includes four general categories: (1) cardiac, (2) pulmonary, (3) mixed cardiac or pulmonary, and (4) noncardiac or nonpulmonary.

Cardiac causes of dyspnea include right, left, or biventricular congestive heart failure with resultant systolic dysfunction, coronary artery disease, recent or remote myocardial infarction, cardiomyopathy, valvular dysfunction, left ventricular hypertrophy with resultant diastolic dysfunction, asymmetric septal hypertrophy, pericarditis, and arrhythmias.

Pulmonary causes include obstructive (e.g., chronic obstructive pulmonary disease (COPD) and asthma) and restrictive processes (e.g., extrapulmonary causes such as obesity, spine or chest wall deformities, and intrinsic pulmonary pathology such as interstitial fibrosis, pneumoconiosis, granulomatous disease or collagen vascular disease).

Mixed cardiac and pulmonary disorders include COPD with pulmonary hypertension and cor pulmonale, deconditioning, pulmonary emboli, and trauma.

Noncardiac or nonpulmonary disorders include metabolic conditions such as anemia, diabetic ketoacidosis and other, less common causes of metabolic acidosis, pain in the chest wall or elsewhere in the body, and neuromuscular disorders such as multiple sclerosis and muscular dystrophy. Obstructive rhinolaryngeal problems include nasal obstruction due to polyps or septal deviation, enlarged tonsils, and supraglottic or subglottic airway stricture.

Dyspnea can also present as a somatic manifestation of psychiatric disorders, e.g., an anxiety disorder, with resultant hyperventilation.

Additional information regarding the evaluation and treatment of dyspnea can be found, e.g., in Morgan and Hodge, Am. Fam. Phys. 57(4):711-718 (1998).

Special Populations

Certain populations of subjects may benefit particularly from the methods described herein. These subjects include people for whom BNP or NT-proBNP alone is less useful, such as in those with impaired renal function (Anwaruddin et al., J. Am. Coll. Cardiol. 47(1):91-7 (2006); McCullough et al., Am. J. Kidney Dis. 41(3):571-9 (2003)), or in those who are overweight (Body Mass Index (BMI) of 25-29) or obese (BMI≧30) (Krauser et al., Am. Heart J. 149(4):744-50 (2005); McCord et al., Arch. Intern. Med. 164(20):2247-52 (2004)). It is known and accepted in the field that patients with a high BMI usually have levels of natriuretic peptide that are lower than expected relative to a normal body mass patient for the same level of disease; the exact mechanism for this phenomenon is not known. It has been shown that circulating levels of ST2 are not influenced by BMI, therefore, the determination of a MACE risk score is more useful than natriuretic peptide levels alone in subjects with high BMI. Thus, the methods described herein can include determining a subject's BMI, and if the subject is overweight or obese, selecting the patient for determination of a MACE risk score, as described herein.

EXAMPLES

The invention is further described in the following examples, which do not limit the scope of the invention described in the claims.

Example 1

Derivation of a Formula Combining ST2 with NT-proBNP for Mace Risk Determination in Patients with Acute Decompensated Heart Failure (HF)

Measurement of either ST2 or NT-proBNP at presentation or at time points during treatment or follow-up have been individually shown to be valuable for prognosis. It has also been determined that the strongest measurement for prognosis is the change in ST2 between two time points. In this analysis forty-eight (48) patients with established symptomatic HF attending two HF clinics with signs and symptoms of worsening HF were evaluated. Baseline (T0) and week 2 (T1) measurements of sST2 and amino-terminal pro-B type natriuretic peptide (NT-proBNP) concentrations were obtained. Adverse cardiac events (death, admission for HF, and heart transplant) were reported in 56% of patients during the 1 year follow-up period. The area under the ROC curve (AUC) values shown in Table 1 calculated for a series of measurements made in this data set illustrate this point when using all cardiac events as the outcome.

TABLE 1

Summary of ROC AUC values for each individual measurement and ratio values for events within 1 year

|  | AUC | SE | 95% CI |
|---|---|---|---|
| ST2_T0 | 0.622 | 0.082 | 0.470 to 0.757 |
| ST2_T1 | 0.583 | 0.0827 | 0.432 to 0.724 |
| NTproBNP_T0 | 0.479 | 0.0845 | 0.333 to 0.628 |
| NTproBNP_T1 | 0.619 | 0.081 | 0.467 to 0.755 |
| ST2_R | 0.772 | 0.0675 | 0.628 to 0.880 |
| NTproBNP_R | 0.717 | 0.0737 | 0.568 to 0.837 |

Using the ST2 ratio in a simple binary stratification approach we get the results shown in Table 2, in this case using the ROC optimal threshold value of 0.75.

TABLE 2

Summary of patient stratification for risk of cardiac events within 1 year using an ST2 ratio threshold of 0.75

|  | ST2 Ratio | | median | mean |
|---|---|---|---|---|
|  | <0.75 | ≧0.75 | 0.875 | 1.030 |
| N | 19 | 29 | | |
| N Event | 6 | 20 | | |
| % Event | 31.6% | 69.0% | | |
| PPV | 69% | | | |
| NPV | 68% | | | |
| RR | 2.2 | | | |

As can be seen in this Table the ROC optimal threshold is lower than either the median or the mean. However if a higher threshold, such as the median value is used, the relative risk decreases to 1.9 so for the purpose of this analysis the threshold of 0.75, which provides the highest prognostic accuracy, will be used.

In other studies (Januzzi et al., J. Am. Coll. Cardiol. 50:607-613 (2007); Mueller et al., Clin. Chim. 54(4):752-756 (2008)) it has also been observed that there is a synergistic relationship between ST2 and NT-proBNP when used for risk stratification or prognosis. In an effort to both confirm that relationship in this cohort and to identify the most powerful method for using ST2 and NT-proBNP together various mathematical combinations were considered. Table 3 represents the best results obtained in a simple binary analysis where the change in ST2 represented as a ratio is combined with the NT-proBNP value at the second time point. The threshold of 0.75 for the ST2 ratio value was determined by ROC analysis, and verified subjectively, to be optimal and an NT-proBNP value of 1000 pg/ml is generally considered ideal for prognosis within a 1 year followup period.

TABLE 3

Summary of patient stratification using the ST2 Ratio and the week 2 NT-proBNP value, using thresholds of 0.75 for the ST2 ratio and 1000 pg/ml for NT-proBNP

| 0.75, 1000 | ST2 R & NTproBNP W2 | | | | | |
|---|---|---|---|---|---|---|
| | ST2−, NT− | ST2−, NT+ | ST2+, NT− | ST2+, NT+ | both− | either+ |
| N | 4 | 15 | 4 | 25 | 4 | 44 |
| N Event | 0 | 6 | 2 | 18 | 0 | 26 |
| % Event | 0.0% | 40.0% | 50.0% | 72.0% | 0.0% | 59.1% |

Although effective at identifying both the highest risk and lowest risk patients, the weakness in this approach is that there is a very small number of patients in the lowest risk group and a large percentage of patients in the indeterminate range.

To better define the functional utility of the ST2 ratio combined with an NT-proBNP value a formula was developed:

$$X = (ST2T1/ST2T0) + \alpha \ln(NTproBNPT1)$$

This formula was developed by evaluating the result as a function of ROC AUC for a range of coefficients associated with the NT-proBNP term. The result from this series of calculations is shown in FIG. 1.

The maximum AUC value was achieved at a coefficient for $\alpha$ of 0.33 resulting in the final equation being:

$$X = (ST2T1/ST2T0) + 0.33 \ln(NTproBNPT1)$$

Figure 2:
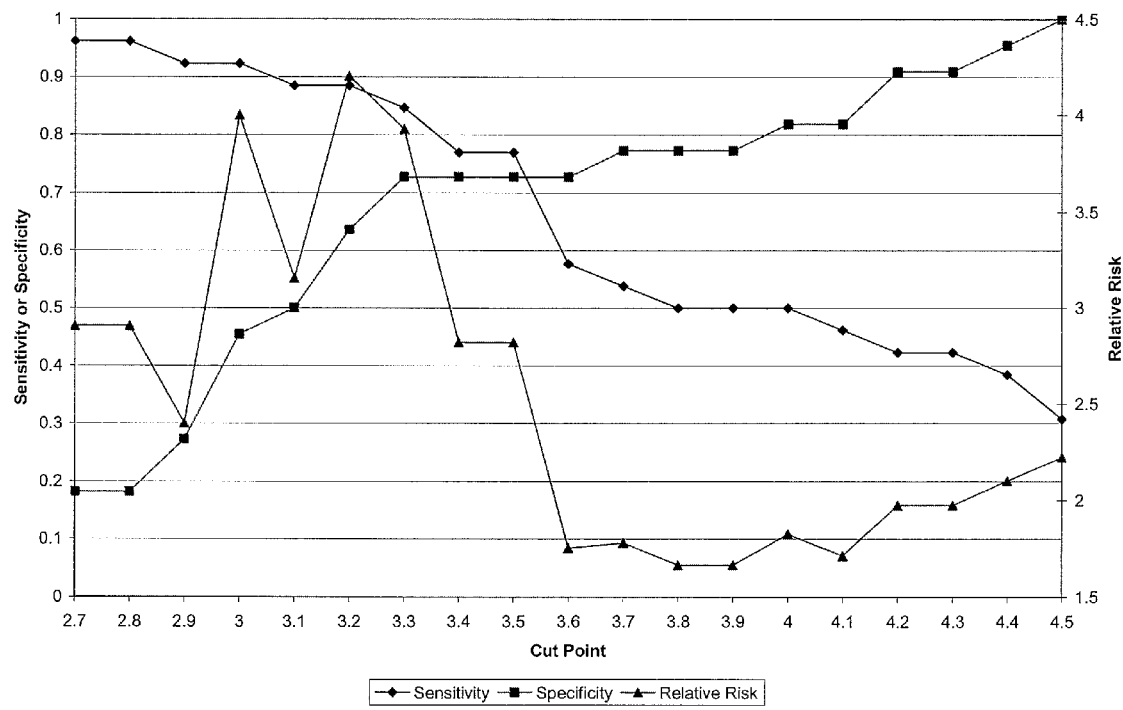
FIG. 2 is a line graph of sensitivity, specificity and relative risk plotted as a function of the score.

Using this algorithm in a series of calculations comparing the sensitivity, specificity and relative risk (right side axis) we get the plot in FIG. 2.

Figure 3:
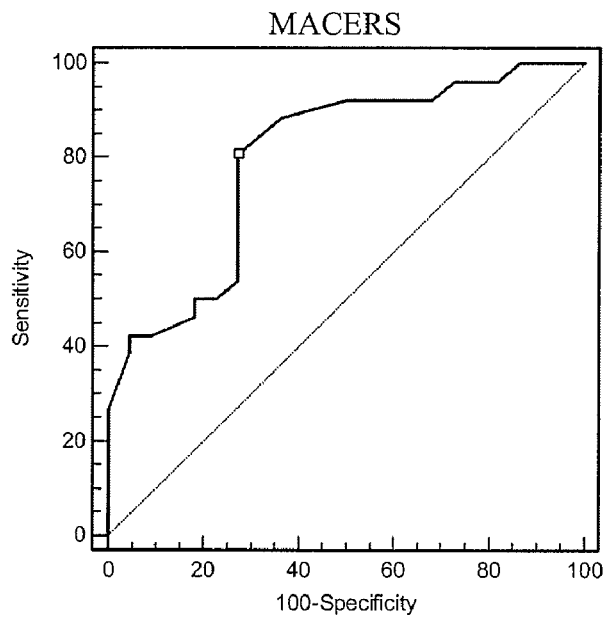
FIG. 3 is a ROC curve for MACE risk score and events within 1 year.

In this plot the score value resulting in the maximum relative risk value is 3.2. ROC analysis of this data confirms that the optimal threshold value is 3.3, illustrated in FIG. 3. Also note that the AUC value using this score is 0.80 as compared to 0.77 for the ST2 ratio and 0.72 for the NT-proBNP ratio, which generated the next highest AUC values.

When this score is used, at the threshold value of 3.2, to stratify patients in this cohort who are at risk of events; admission, transplant or mortality, a clear distinction between low risk and high risk patients is achieved. These results are illustrated in Table 4.

TABLE 4

Summary of patient stratification for risk of adverse events within 1 year using a score cutpoint of 3.2

| | Score | | median | mean |
|---|---|---|---|---|
| | <3.2 | ≥3.2 | 3.55 | 3.71 |
| N | 17 | 31 | | |
| N Event | 3 | 23 | | |
| % Event | 17.6% | 74.2% | | |
| PPV | 74.2% | | | |
| NPV | 82.4% | | | |
| RR | 4.2 | | | |

Directly comparing these results with the results using the ST2 ratio alone, shown in Table 2, illustrates that by combining the ST2 ratio with an NT-proBNP value all of the relevant parameters representing assessment of risk prediction are stronger; PPV, NPV and RR.

For comparison the stratification results for the next strongest value, the NT-proBNP ratio is summarized in Table 5. The values using the NT-proBNP ratio are much lower than when the ST2 ratio is used or from the formula combining ST2 with NT-proBNP.

TABLE 5

Summary of patient stratification for risk of adverse events within 1 year using the NT-proBNP ratio

| | NT-proBNP Ratio | | median | mean |
|---|---|---|---|---|
| | <0.75 | ≥0.75 | 0.74 | 0.83 |
| N | 24 | 24 | | |
| N Event | 10 | 16 | | |
| % Event | 41.7% | 66.7% | | |
| PPV | 66.7% | | | |
| NPV | 58.3% | | | |
| RR | 1.1 | | | |

TABLE 6

Comparison of ST2 Ratio and Score Values

| | NTproBNP Ratio | ST2 Ratio | Score |
|---|---|---|---|
| PPV | 67% | 69% | 74% |
| NPV | 58% | 68% | 82% |
| RR | 1.1 | 2.2 | 4.2 |

Figure 4A:
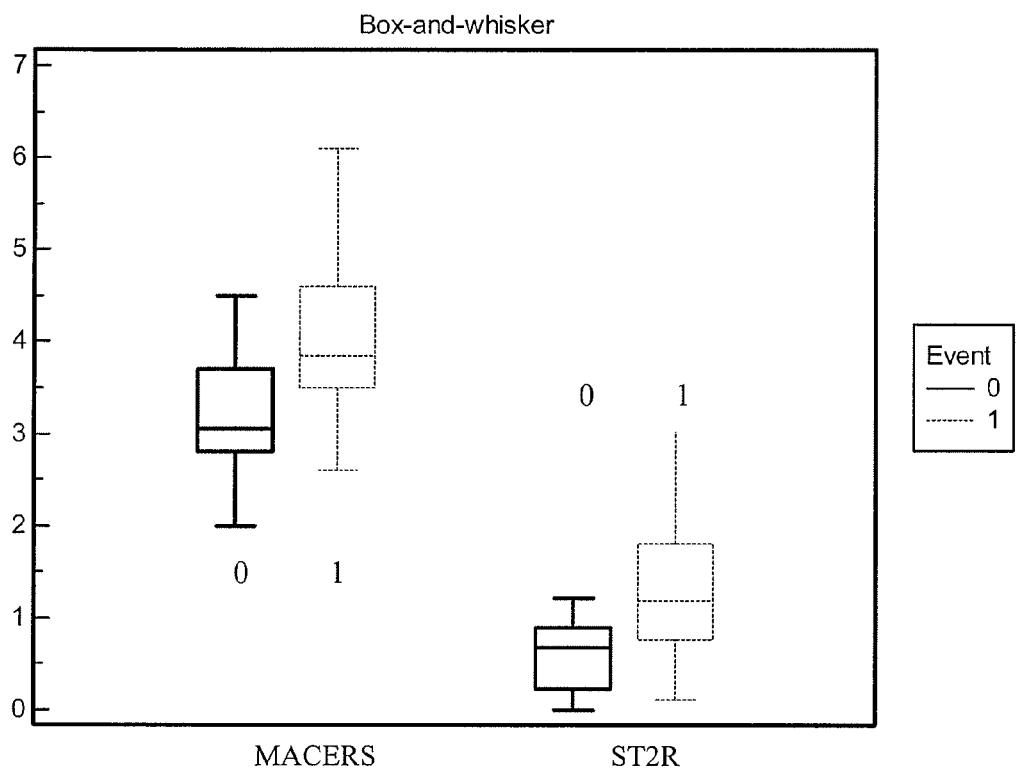
FIG. 4A is a whisker box plot of MACE risk score and ST2 ratio for cardiac events within 1 year.

The relative differences between the score and ST2 ratio values can also be represented graphically using whisker box plots, as shown in FIG. 4A. As expected, both groups had statistically significant resolution between the event and no event clusters, P=0.0004 for Score and P=0.0013 for ST2 ratio.

Figure 4B:
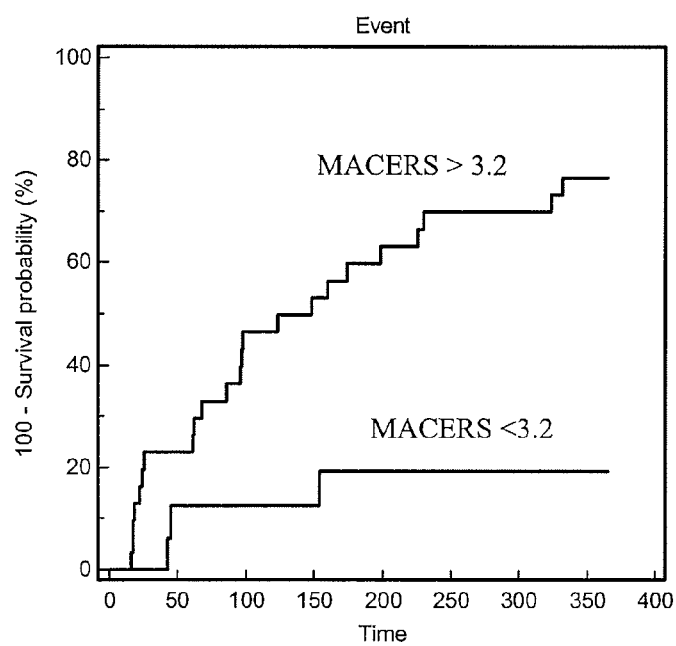
FIG. 4B is a Kaplan-Meier Survival Curve for events using MACE risk score at a threshold of 3.2.
Figure 5:
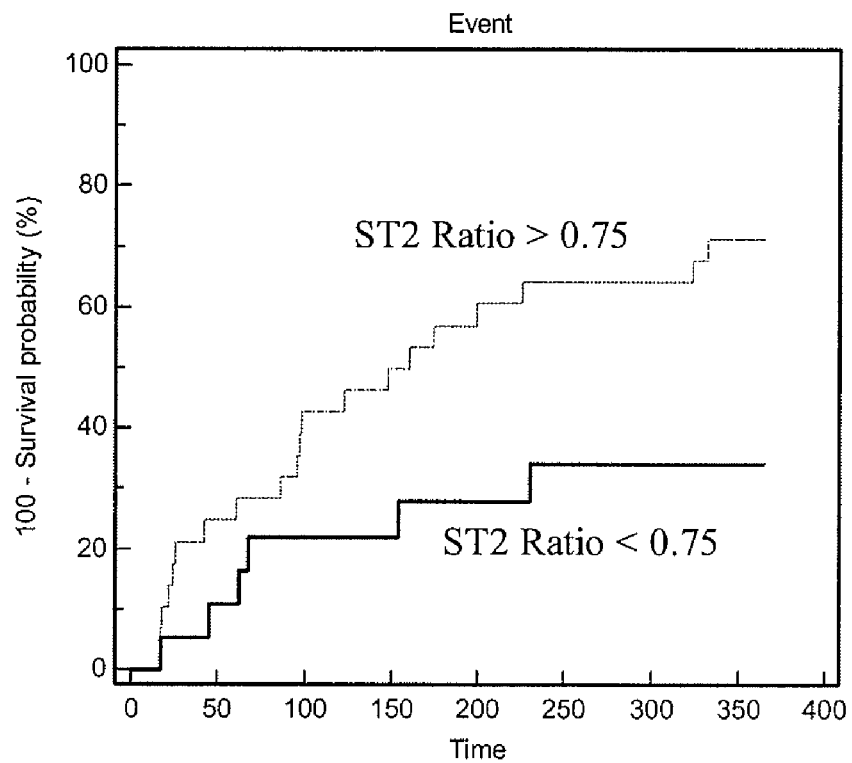
FIG. 5 is a Kaplan-Meier Survival Curve for events using the ST2 ratio.
Figure 6:
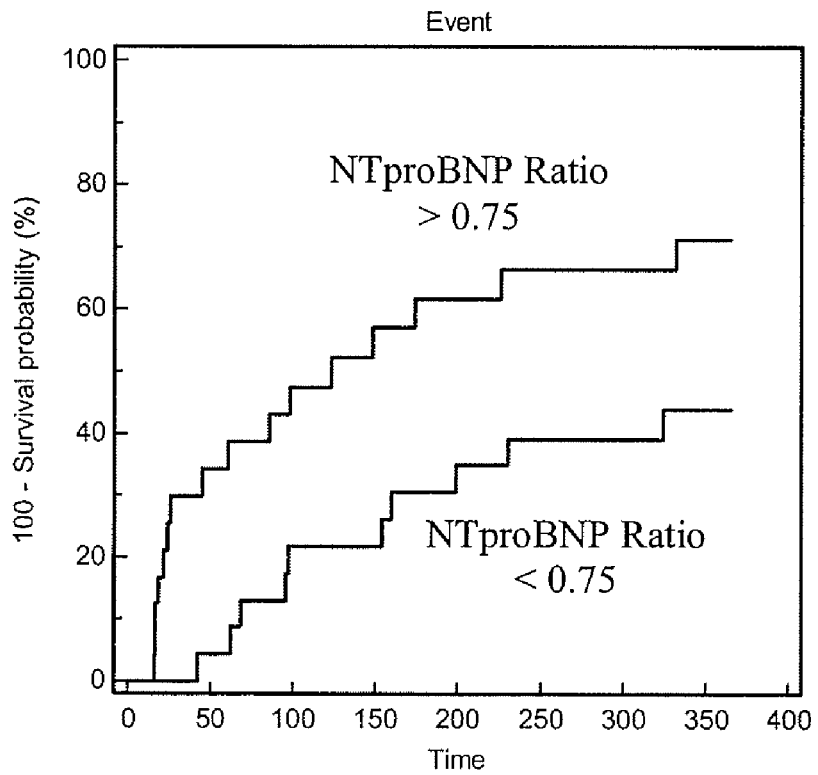
FIG. 6 is a Kaplan-Meier Survival Curve for events using NT-proBNP ratio at a threshold of 0.75.
Figure 7:
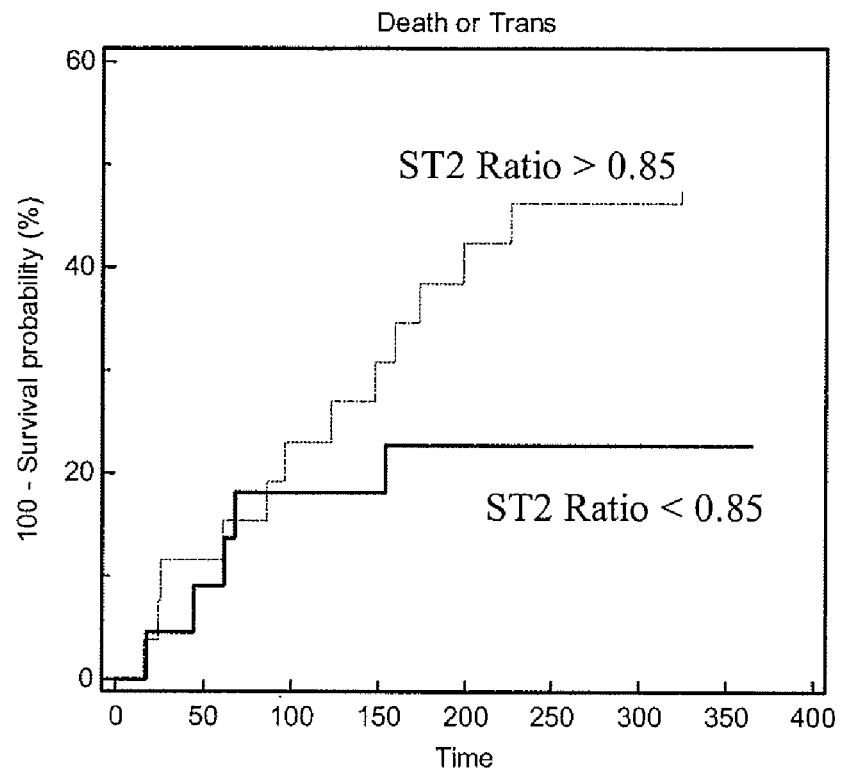
FIG. 7 is a Kaplan-Meier Survival Curve for death or transplant within 1 year using ST2 ratio at a threshold of 0.85.
Figure 8:
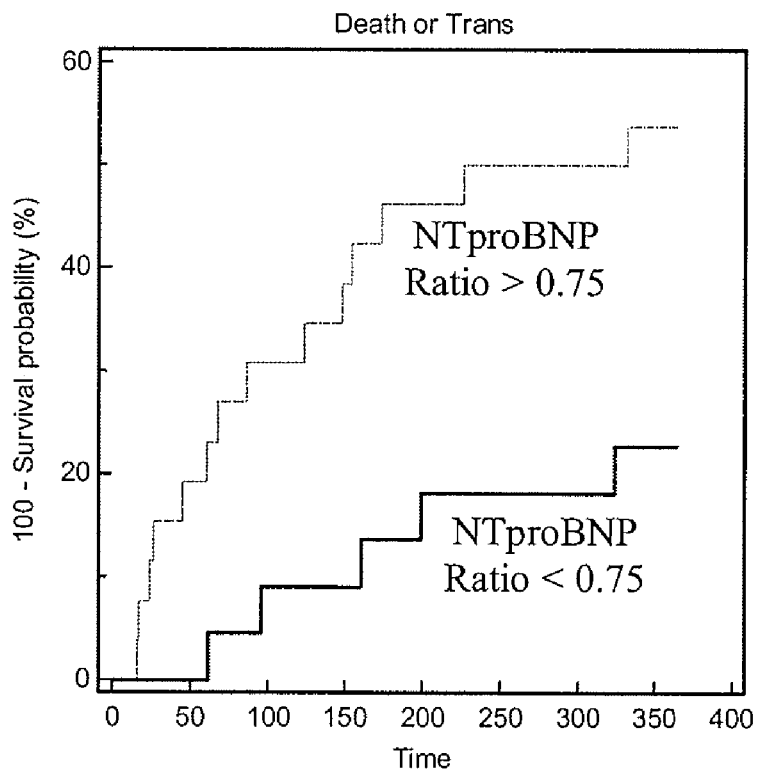
FIG. 8 is a Kaplan-Meier Survival Curve for death or transplant within 1 year using NT-proBNP ratio at a threshold of 0.70.

The distinction between the score generated from this formula and the ratio for ST2 values is also observed when analyzed by Kaplan-Meier survival curves. FIG. 4B shows the survival curve results for the formula score with a calculated hazard ratio of 5.93. Consistent with the previous calculations, FIG. 5 shows that this same analysis for the ST2 ratio had a hazard ratio of 2.72, which is similar to the value calculated for the NT-proBNP ratio of 2.39, as shown in FIG. 6.

The hazard ratios calculated from the Kaplan-Meier curves was consistent with the Cox proportional-hazards regression analysis. Table 7 summarizes the hazard ratio (HR) values from both calculations for the three most informative measurements.

TABLE 7

Summary of hazard ratio values for risk of event at 1 year followup

|  | CCD Score | | ST2 ratio | | NT-proBNP ratio | |
|---|---|---|---|---|---|---|
|  | HR | p | HR | p | HR | p |
| K-M curve | 5.93 | 0.0009 | 2.72 | 0.025 | 2.39 | 0.025 |
| cox | 6.07 | 0.003 | 2.73 | 0.03 | 2.12 | 0.059 |

This formula was also evaluated for accuracy in predicting the more definitive endpoints of death and/or transplant, as shown in Table 8.

TABLE 8

Summary of ROC AUC values for each individual measurement and ratio values for death or transplant within 1 year

|  | AUC | SE | 95% CI |
|---|---|---|---|
| ST2_S0 | 0.625 | 0.0813 | 0.474 to 0.761 |
| ST2_S2 | 0.521 | 0.0858 | 0.372 to 0.667 |
| NTPROBNP_S0 | 0.564 | 0.086 | 0.414 to 0.707 |
| NTPROBNPS2 | 0.679 | 0.0813 | 0.528 to 0.806 |
| ST2_R | 0.706 | 0.0793 | 0.557 to 0.828 |
| NTPROBNP_R | 0.672 | 0.0818 | 0.521 to 0.800 |

In this analysis, the only variable that had an AUC greater than 0.7 is the ST2 ratio. For the outcome of death or transplant a threshold value of 0.85 for the ST2 ratio was determined by ROC analysis to be optimal, as shown in Table 9.

TABLE 9

ST2 Ratio ROC Values

| Criterion | Sensitivity | 95% CI | Specificity | 95% CI | +LR | −LR |
|---|---|---|---|---|---|---|
| >0.85 | 68.42 | 43.5-87.3 | 58.62 | 38.9-76.5 | 1.65 | 0.54 |

When these results were compared to a generally accepted threshold value for a change in NT-proBNP of 0.7 (the ROC optimal value for the NT-proBNP ratio is 0.58), the results shown in Table 10 were generated. Note that the optimal threshold value for the ST2 ratio and risk of death or transplant within 1 year was higher at 0.85 than the optimal threshold value of 0.75 for any adverse cardiac event within 1 year.

TABLE 10

Summary of patient stratification for risk of death or transplant within 1 year comparing the ST2 ratio and the NT-proBNP ratio

|  | ST2 Ratio | | NT-proBNP Ratio | |
|---|---|---|---|---|
|  | <0.85 | ≥0.85 | <0.7 | ≥0.7 |
| N | 22 | 26 | 22 | 26 |
| N Event | 5 | 14 | 5 | 14 |
| % Event | 22.7% | 53.8% | 23% | 54% |
| PPV |  | 53.8% |  | 53.8% |
| NPV | 77.3% |  | 77.3% |  |
| RR |  | 2.4 |  | 2.4 |

Although each biomarker had similar predictive strength, of the five patients identified below the threshold, only one was predicted by both biomarkers.

Kaplan-Meier survival curve analysis also showed that, when considered individually in this population, the ST2 ratio and the NT-proBNP ratio were functionally indistinguishable in regards to outcome prediction, although the curve for the NT-proBNP ratio diverges early and remains divergent, whereas the curve for the ST2 ratio diverges much later. For the ST2 ratio the HR is 2.66 (p=0.0506), while for the NT-proBNP ratio the HR is 2.60 (P=0.0201).

The results obtained by Cox proportional-hazards regression analysis are slightly different. When analyzed individually the HR values were 1.94 for the ST2 ratio and 0.55 for the NT-proBNP ratio, and were almost the same when analyzed together at 2.03 for the ST2 ratio and 0.53 for the NT-proBNP ratio. The p value was not significant for either variable, at 0.176 and 0.168 respectively.

Figure 9:
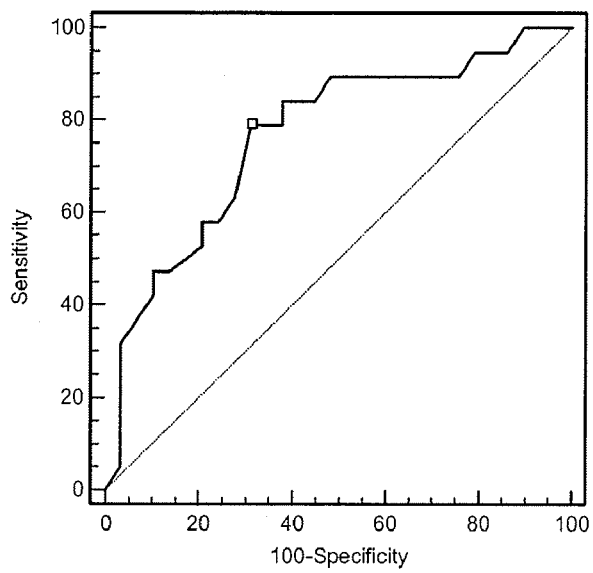
FIG. 9 is a ROC curve for Score and death or transplant within 1 year. Although ROC analysis identifies 3.5 as the optimal threshold, additional analysis confirms that the previously identified threshold of 3.2 provides better prognostic accuracy.

However, as was observed when events were evaluated as the outcome parameter, if the ST2 ratio was combined with the second NT-proBNP value the results of ROC analysis illustrate greater predictive accuracy using this formula, as shown in FIG. 9.

Figure 10:
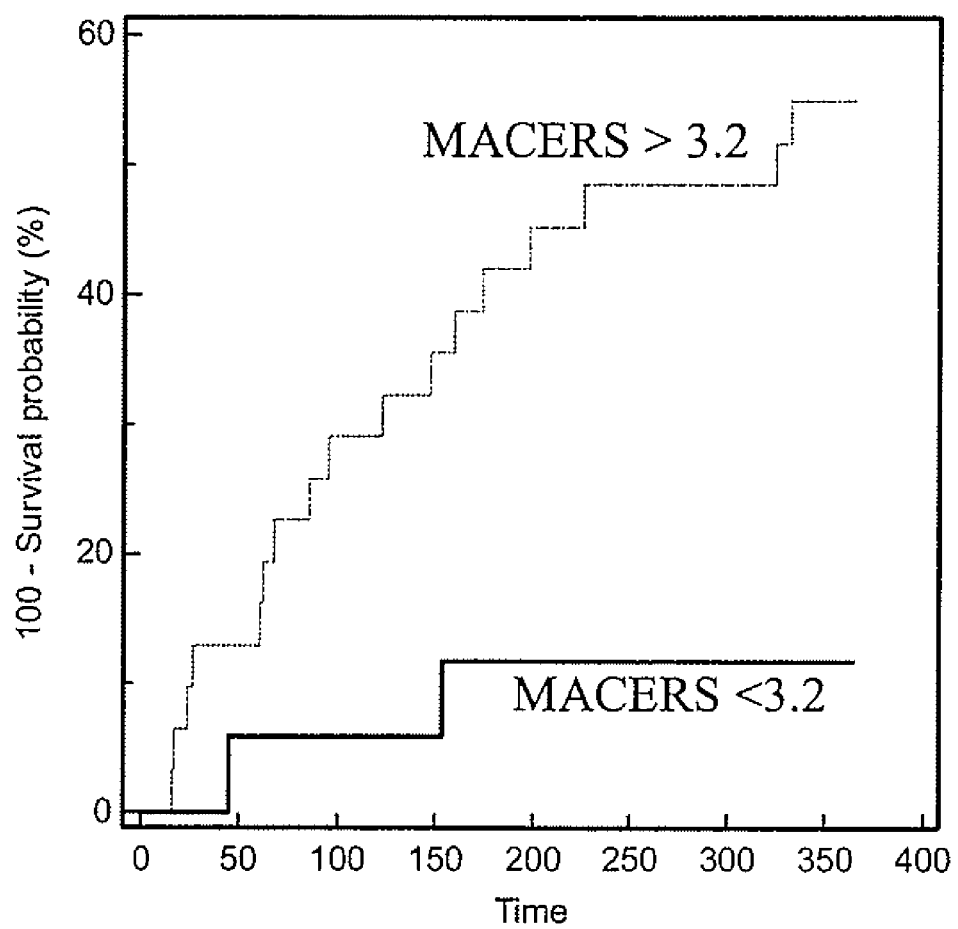
FIG. 10 is a Kaplan-Meier Survival Curve for death or transplant within 1 year using the MACE risk score at the threshold of 3.2.

Although ROC analysis identified 3.5 as the optimal threshold, additional analysis confirms that the previously identified threshold of 3.2 provides better prognostic accuracy. The HR from Kaplan-Meier survival analysis (FIG. 10) was 6.02 (p=0.0060). The HR calculated from the Cox proportional-hazards regression analysis was very similar at 6.08 (p=0.016).

Table 11 provides a summary of relative risk calculations comparing the values previously determined for the ST2 and NT-proBNP ratios as well as the MACE risk score.

TABLE 11

Summary of patient stratification for risk of death or transplant within 1 year
Death or Transplant within 1 Year

|  | ST2 Ratio | | NT-proBNP Ratio | | MACE risk score | |
|---|---|---|---|---|---|---|
|  | <0.85 | ≥0.85 | <0.7 | ≥0.7 | <3.2 | ≥3.2 |
| N | 22 | 26 | 22 | 26 | 17 | 31 |
| N Event | 5 | 14 | 5 | 14 | 2 | 17 |
| % Event | 22.7% | 53.8% | 23% | 54% | 11.8% | 54.8% |
| PPV |  | 53.8% |  | 53.8% |  | 54.8% |
| NPV | 77.3% |  | 77.3% |  | 88.2% |  |
| RR |  | 2.4 |  | 2.4 |  | 4.7 |

Figure 11:
FIG. 11 is a whisker box plot showing MACE risk score for events or no-events (death or transplant).
Figure 12:
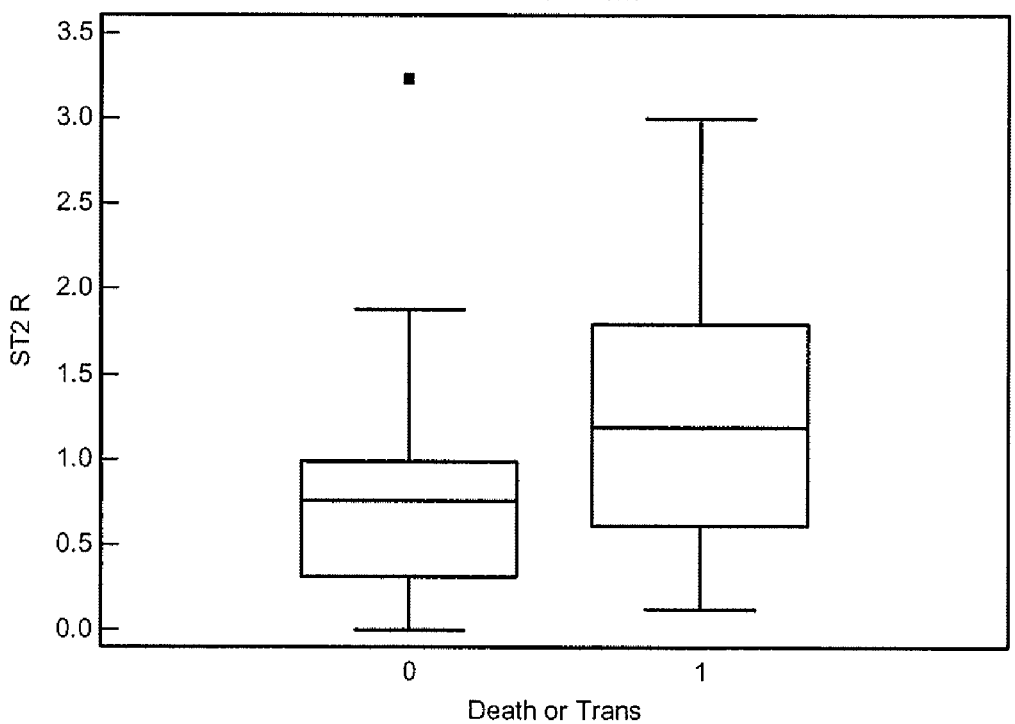
FIG. 12 is a whisker box plot showing ST2 ratio for events or no-events (death or transplant).
Figure 13:
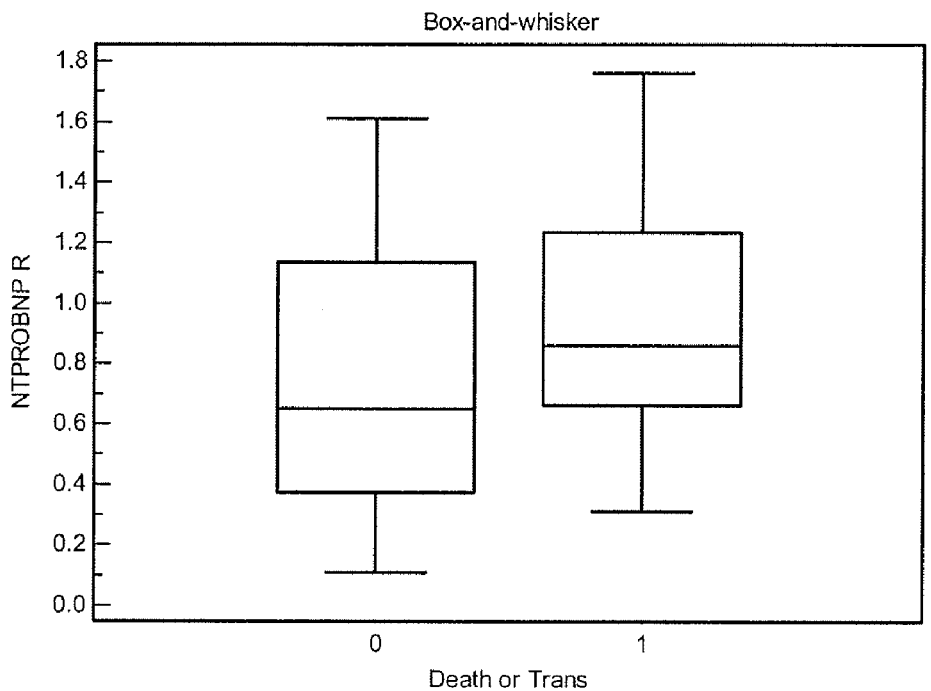
FIG. 13 is a whisker box plot showing NT-proBNP ratio for events or no-events (death or transplant).

A simple box plot (FIG. 11) illustration confirms the distinction between the event and non-event group for the MACE risk score values. For this plot p=0.002. Note that the median values do not overlap with the 25-75% boundary. This same comparison for the ST2 ratio and the NT-proBNP ratio is shown in FIGS. 12 and 13. The p values for these plots are 0.017 and 0.046 respectively and the distinction between the event and no-event group is not as definitive as it is for the MACE risk score.

Conclusion

As derived from this data set, the described formula combining the ratio of ST2 values between two time points and an NT-proBNP value measured at the second time point provides the strongest and most accurate measure of risk that a patient will experience an adverse cardiac event defined as admission, transplant or death.

Example 2

Validation Analysis of the Formula Combining ST2 with NT-proBNP for Mace Risk Prediction In the study described in this example, 150 patients hospitalized with acutely destabilized HF were followed at the Veteran Affairs Healthcare System in San Diego, Calif. Multiple cardiac-related parameters were measured, including ST2, BNP, NT-proBNP, and blood urea nitrogen (BUN). Plasma samples were collected at six time points between admission and discharge. Biomarker concentrations were correlated to survival at 90 days. These 150 patients were sorted further by the following criteria to optimize coordination between the various measurements that were made and the times that these measurements were made:

1. ST2 value on day 1
2. ST2 value on day 3 or later for a minimum elapsed time of 2 days
3. NT-proBNP value on the same last day as the last ST2 value
4. Alive at discharge This sort resulted in a total remaining N of 107 patients, with 35 events, readmission or death, within 90 days and 13 of those events were deaths within 90 days. The following analysis compares the various individual measurements for accuracy in predicting mortality within 90 days and validates the formula combining ST2 with NT-proBNP.

Figure 14:
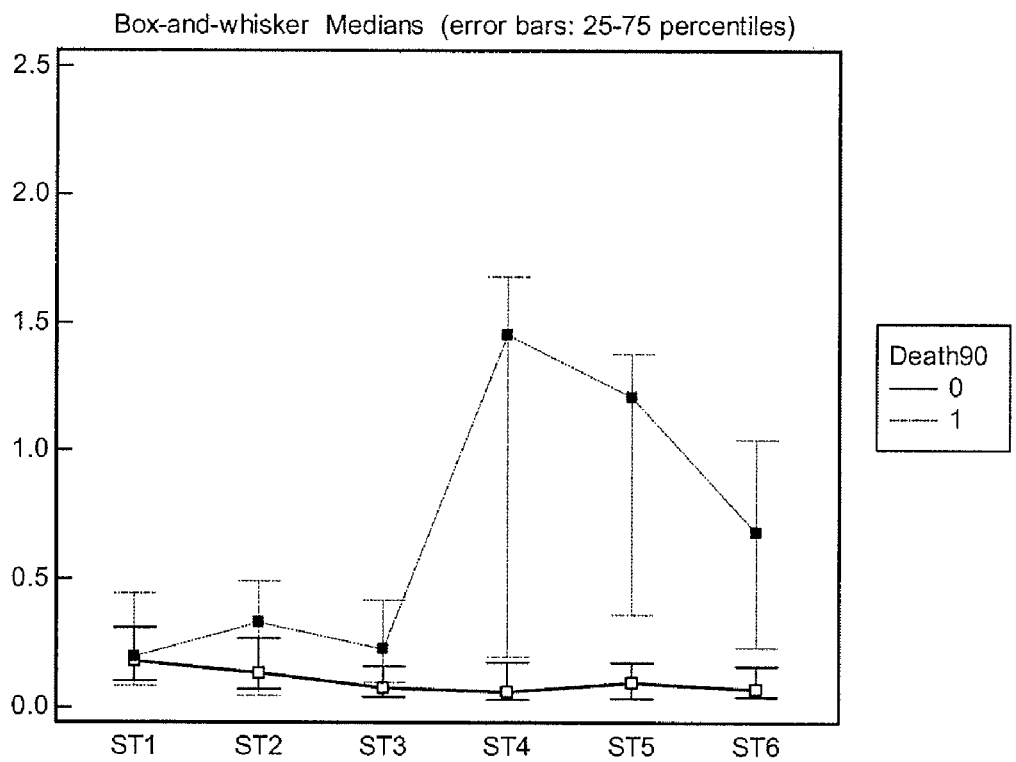
FIG. 14 is a whisker and dot plot showing ST2 values by days.
Figure 15:
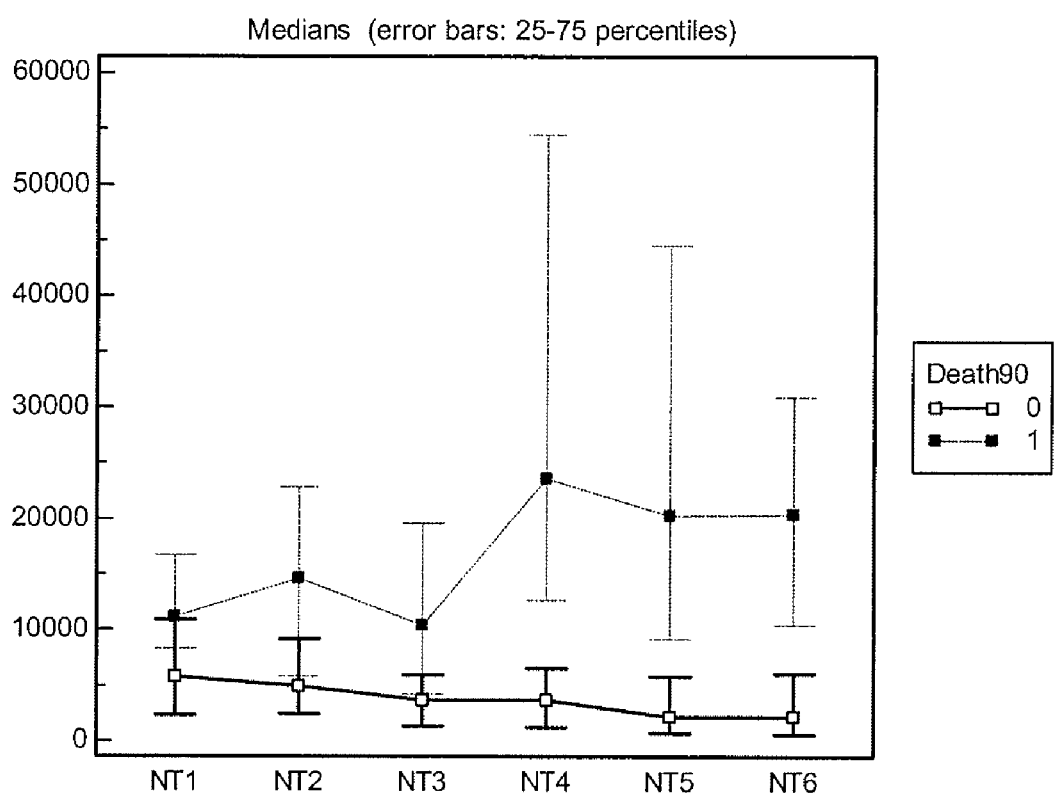
FIG. 15 is a whisker and dot plot showing NT-proBNP values by day.
Figure 16:
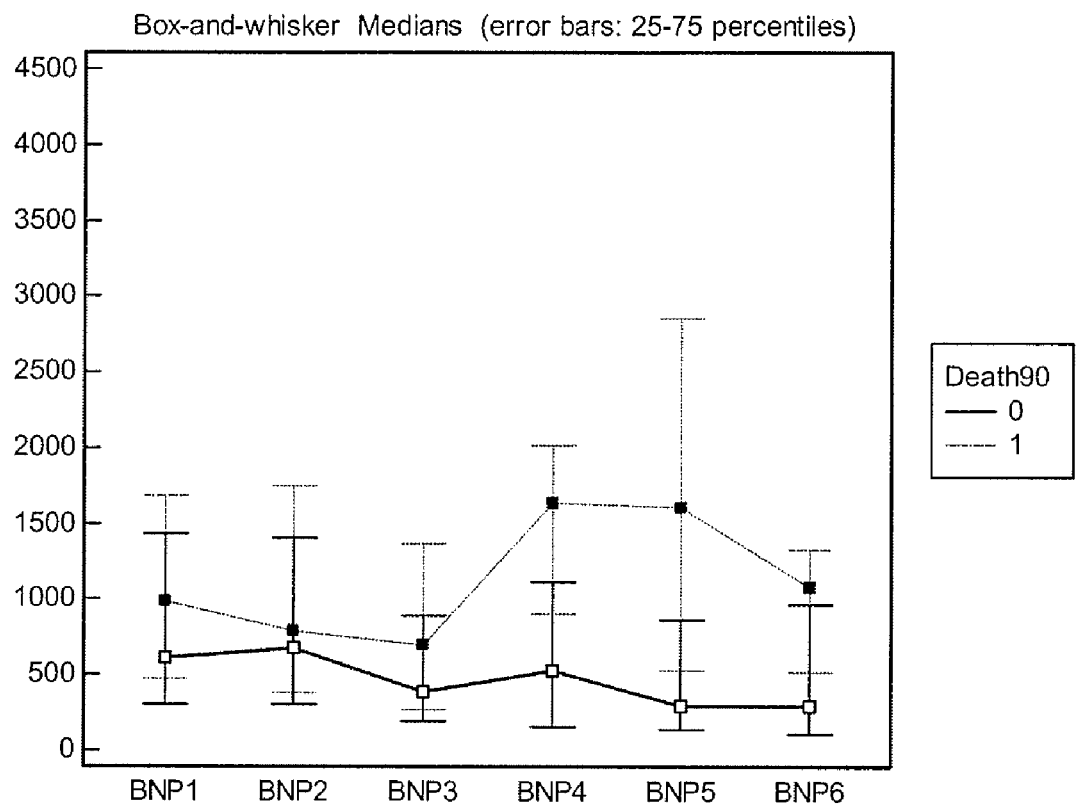
FIG. 16 is a whisker and dot plot showing BNP values by day.

If the biomarkers are reported by day and as a function of whether the patient survived or died there is a clear distinction over time. In patients who did not survive the values for ST2, as well as BNP and NT-proBNP increased, whereas in those patients who did survive these values decreased and remained low. In FIGS. 14-16, the median is plotted with error bars representing the $25^{th}$-$75^{th}$ percentiles.

In this analysis, by day four (three elapsed days), all three biomarkers achieved maximum separation in median values between survivors and decedents, but only ST2 and NT-proBNP were also able to achieve and maintain significant resolution not only between the median values but also between the $25^{th}$-$75^{th}$ percentile values.

ROC analysis, summarized in Table 13, affirmed this observation with maximum AUC values for each biomarker at either the individual day 4 measurement or of the change, reported as a ratio, between baseline and day 4. However, the functional strength of using the measurements from day 4 was limited in this instance because from this cohort of 107 patients there were only 60 values reported for day 4. To maximize the number of patients that were included in the analysis, a value for last (L) was obtained by taking the last value available for each patient from day 3 or later. It is noted that the AUC values for the last value were not significantly different than the values for the day 4 value from each biomarker, nor were the AUC values for the ratio of the 4:1 measurements or the L:F measurements. Consequently, for the remainder of this analysis the values used were the first (1), last (L) and the last to first (L:F) ratio.

TABLE 13

Individual AUC values from ROC analysis for mortality within 90 days

| | AUC Death 90 |
|---|---|
| BNP 1 | 0.602 |
| BNP 4 | 0.739 |
| BNP L | 0.729 |
| BNP R 4:1 | 0.684 |
| BNP R L:F | 0.684 |
| NTproBNP 1 | 0.735 |
| NTproBNP 4 | 0.836 |
| NTproBNP L | 0.824 |
| NTproBNP R 4:1 | 0.820 |
| NTproBNP R L:F | 0.776 |
| ST2 1 | 0.530 |

TABLE 13-continued

Individual AUC values from ROC analysis for mortality within 90 days

| | AUC Death 90 |
|---|---|
| ST2 4 | 0.889 |
| ST2 L | 0.773 |
| ST2 R 4:1 | 0.816 |
| ST2 R L:F | 0.838 |
| BUN | 0.830 |

Figure 17:
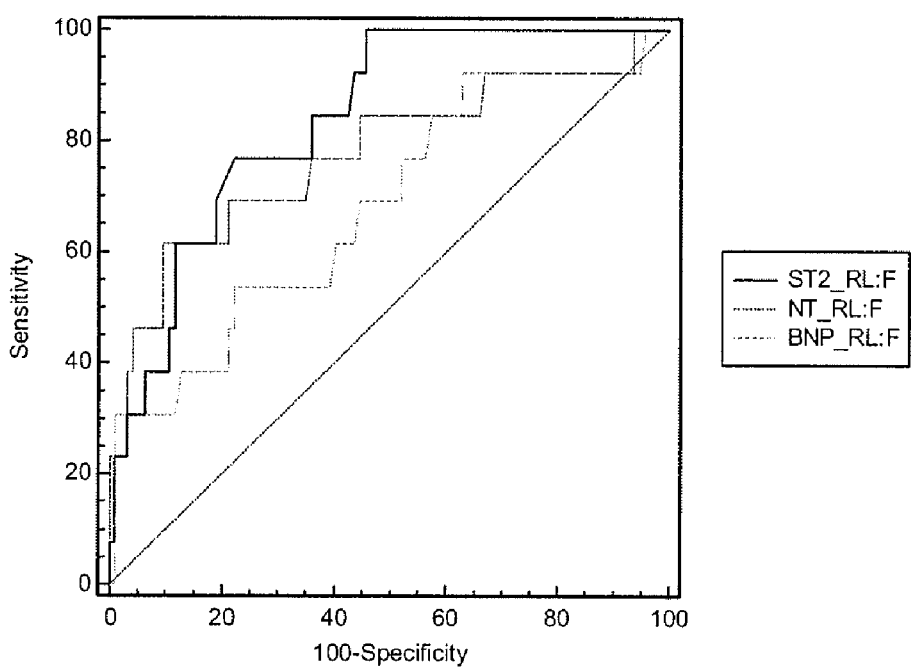
FIG. 17 is a line graph showing the results of ROC analysis of ratio values for mortality within 90 days.

FIG. 17 and Table 14 summarizes the ROC analysis for the L:F ratio values for each biomarker. In pairwise comparison none of the curves achieves statistically significant resolution.

TABLE 14

ROC analysis results of ratios for mortality within 90 days

| | AUC | SE | 95% CI |
|---|---|---|---|
| ST2_RL_F | 0.838 | 0.0708 | 0.754 to 0.902 |
| NT_RL_F | 0.776 | 0.079 | 0.685 to 0.851 |
| BNP_RL_F | 0.684 | 0.0859 | 0.587 to 0.770 |

Figure 18:
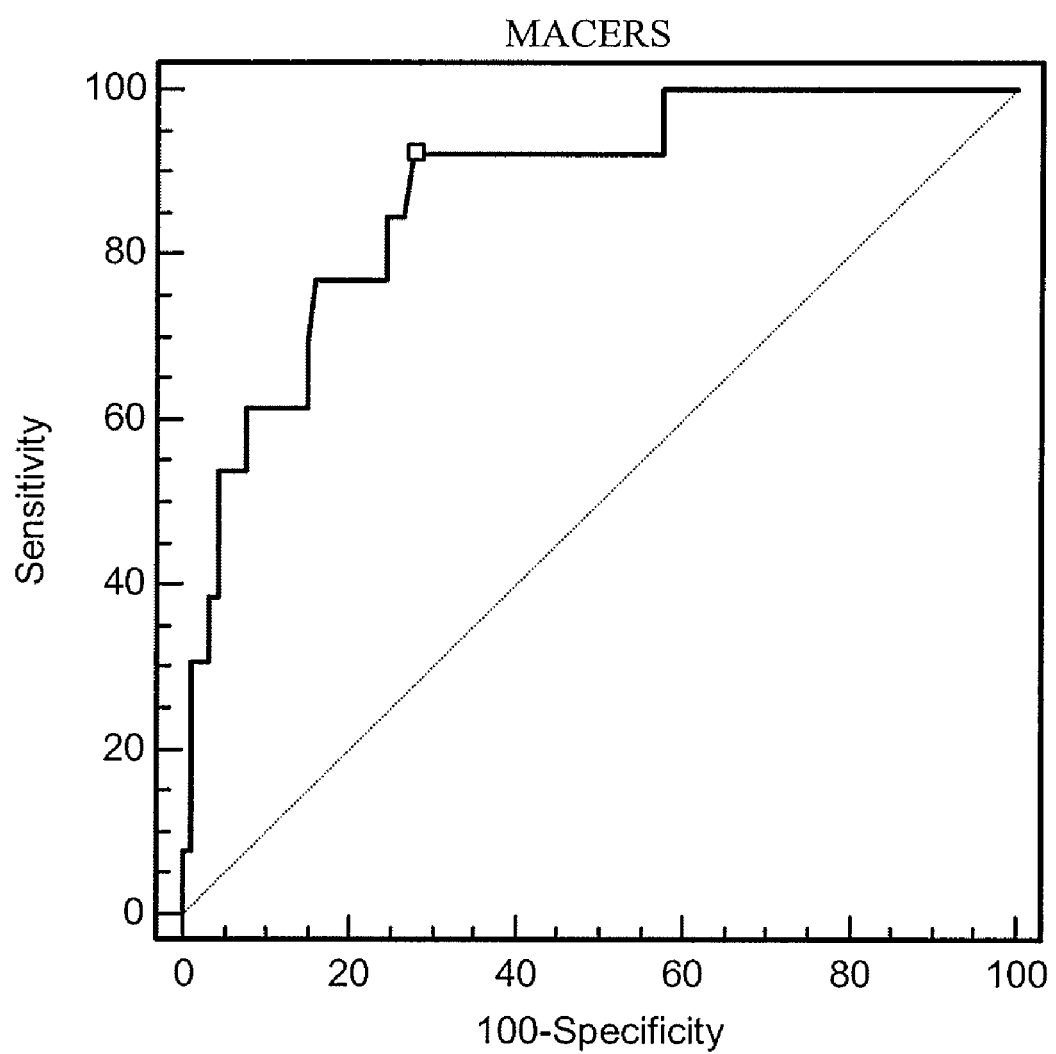
FIG. 18 is a line graph showing MACE risk formula ROC for mortality within 90 days.

As was determined using the peptide cohort data for derivation, the mortality risk score formula result yielded a ROC analysis AUC greater than any of the individual measurements or the ratio values. The ROC analysis for this formula is shown in FIG. 18 and the ROC analysis data summarized in Table 15.

TABLE 15

MACE risk score formula ROC data for mortality within 90 days

Positive group

Death90 = 1
Sample size 13

Negative group

Death90 = 0
Sample size 94
Area under the ROC curve (AUC)  0.876
Standard error  0.0639
95% Confidence interval  0.798 to 0.931
Significance level P (Area = 0.5)  0.0001

Criteron Values and coordinates of the ROC curve

| Criterion | Sensitivity | 95% CI | Specificity | 95% CI | +LR | −LR |
|---|---|---|---|---|---|---|
| >=1.67 | 100.00 | 75.1-100.0 | 0.00 | 0.0-3.9 | 1.00 | |
| >3.1 | 100.00 | 75.1-100.0 | 42.55 | 32.4-53.2 | 1.74 | 0.00 |
| >3.12 | 92.31 | 63.9-98.7 | 42.55 | 32.4-53.2 | 1.61 | 0.18 |
| >3.52 * | 92.31 | 63.9-98.7 | 72.34 | 62.2-81.1 | 3.34 | 0.11 |
| >3.59 | 84.62 | 54.5-97.6 | 73.40 | 63.3-82.0 | 3.18 | 0.21 |
| >3.61 | 84.62 | 54.5-97.6 | 75.53 | 65.6-83.8 | 3.46 | 0.20 |
| >3.62 | 76.92 | 46.2-94.7 | 75.53 | 65.6-83.8 | 3.14 | 0.31 |
| >3.75 | 76.92 | 46.2-94.7 | 84.04 | 75.0-90.8 | 4.82 | 0.27 |

Figure 19:
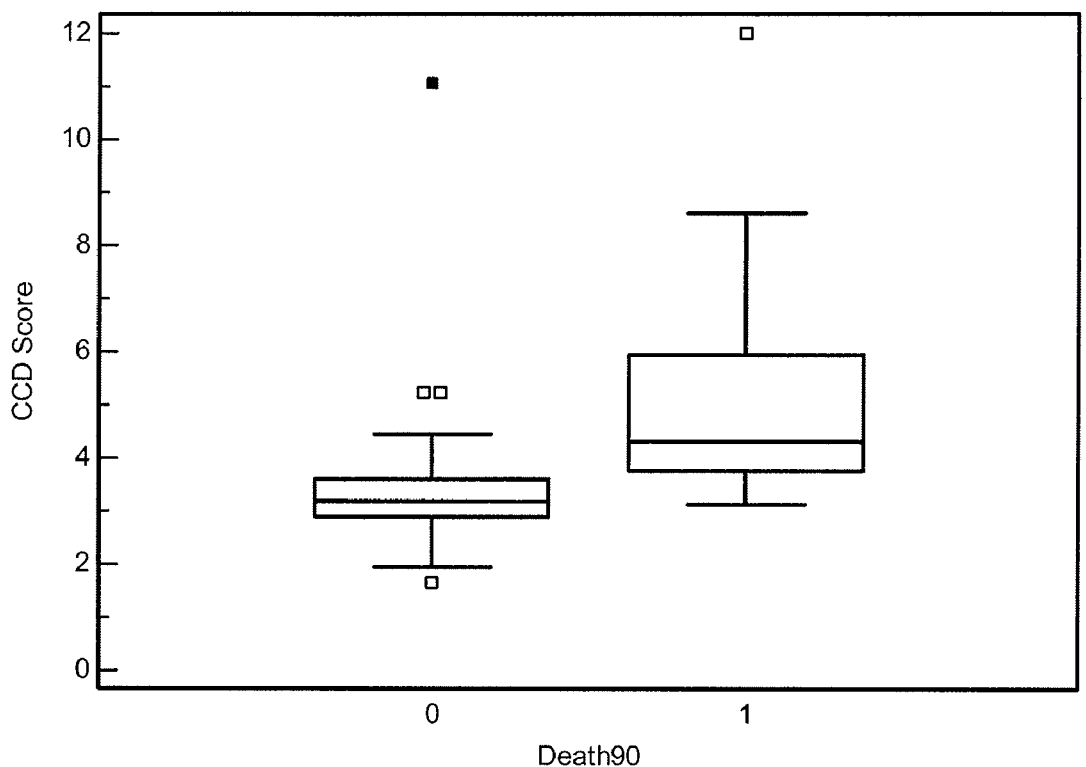
FIG. 19 is a whisker box plot showing MACE risk formula score for mortality within 90 days.
Figure 20:
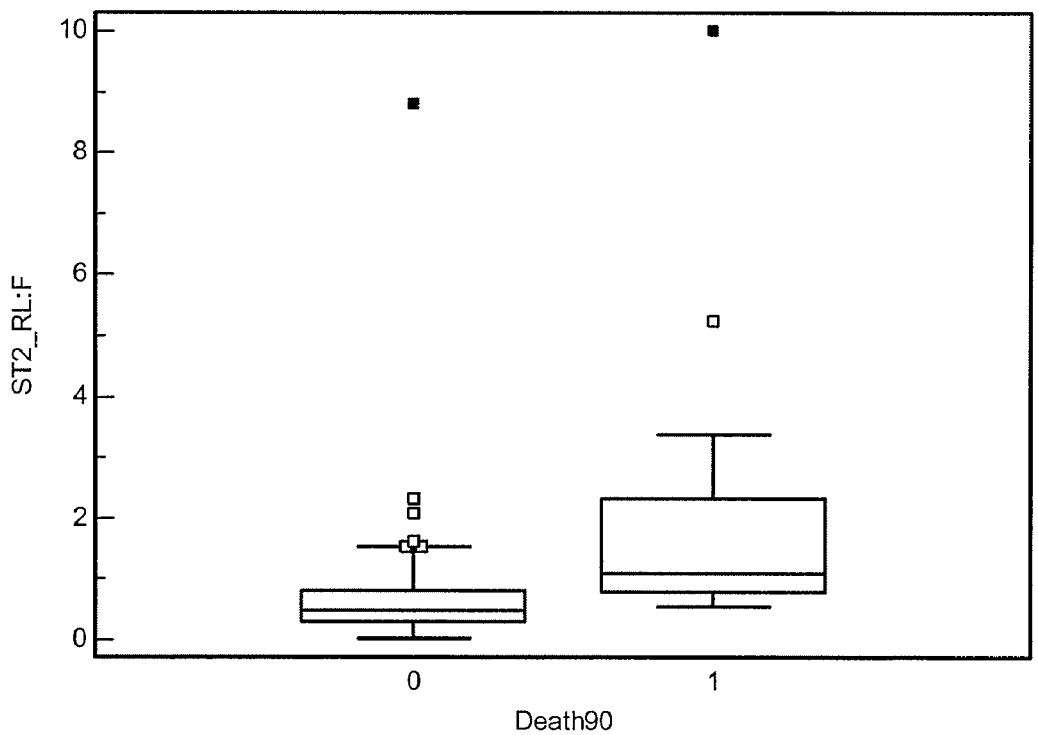
FIG. 20 is a whisker box plot showing ST2 R L:F for mortality within 90 days.

The ROC optimal value from this analysis was 3.52. As was noted using the peptide cohort data (see Example 1), the MACE risk score formula ROC optimal was also 3.5 but the best prognostic (mortality) accuracy was achieved with a value of 3.2 in that cohort. A basic whisker box plot (FIG. 19) shows clear resolution between the survivor and decedent groups, p<0.0001. For comparison, a whisker box plot analysis of the ST2 R L:F is similar, with a p=0.0001 (FIG. 20). As was also noted using the peptide cohort data a basic matrix analysis and relative risk calculation confirms that the MACE risk score provides the most accurate mortality prediction.

TABLE 16

Matrix and relative risk analysis of the strongest mortality prediction variables

|  | ST2 R L:F | | NTproBNP R L:F | | MACE risk score | |
| --- | --- | --- | --- | --- | --- | --- |
|  | <0.85 | ≧0.85 | <0.7 | ≧0.7 | <3.5 | ≧3.5 |
| N | 76 | 31 | 49 | 58 | 65 | 42 |
| N mortality | 3 | 10 | 2 | 11 | 1 | 12 |
| % mortality | 3.9% | 32.3% | 4.1% | 19.0% | 1.5% | 28.6% |
| PPV |  | 32.3% |  | 19.0% |  | 28.6% |
| NPV | 96.1% |  | 95.9% |  | 98.5% |  |
| RR |  | 8.2 |  | 4.6 |  | 18.6 |

Although both the ST2 ratio and the NTproBNP ratio yielded good relative risk values, the relative risk using the MACE risk score was much higher.

Conclusion

As was determined using the peptide cohort data (Example 1) the MACE risk score formula described herein provides the greatest prognostic accuracy, specifically when the outcome parameter is mortality, as determined by ROC, hazard ratio and relative risk calculation. There is a small but likely significant difference between the threshold values in these two cohorts. The peptide cohort described in Example 1 is an outpatient group with an ST2 ratio threshold of 0.75 and a MACE risk score formula threshold of 3.2, whereas the VET cohort described in this Example 2 is an inpatient group, and the respective threshold values are 0.85 and 3.5. This difference in threshold values may be due to the difference in disease severity between inpatient and outpatient conditions or may be due to the difference in time between measurements, as there was a 2 week time frame between measurements in the outpatient cohort as compared to a 3-5 day time frame in the inpatient cohort. Shimpo et al., Circulation 109 (18):2186-90 (2004), reported that ST2 values increase rapidly for the first 12 hours following a myocardial infarction. The results described in these two examples clearly illustrate that there is also a dynamic change in ST2 levels in patients with heart failure but the absolute kinetic parameters are yet to be determined.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for evaluating a subject's risk of a major adverse cardiac event (MACE) within one year, the method comprising:
   determining a first level of soluble Growth Stimulation-Expressed Gene 2 (ST2) in a biological sample obtained from a subject at a first time point (ST2T0), a second level of soluble ST2 in a biological sample obtained from a subject at a second time point (ST2T1), and a level of natriuretic peptide (NP) in a biological sample obtained from a subject at the second time point (NPT1);
   determining a MACE risk score (MACERS) for a subject utilizing, at least in part, a ratio of ST2T1 to ST2T0, in combination with a weighted logarithm of NPT1, and comparing the MACERS to a reference MACERS;
   wherein the MACERS in comparison with the reference MACERS is indicative of the subject's risk of a MACE within one year.

2. The method of claim 1, wherein the logarithm of NPT1 includes a natural logarithm.

3. The method of claim 1, wherein the MACERS is determined using the following formula:

$$MACERS = (ST2T1/ST2T0) + \alpha \ln(NPT1),$$

wherein the coefficient $\alpha$ is a weighting factor for the variable it acts on.

4. The method of claim 3, wherein the coefficient $\alpha$ is about 0.33.

5. The method of claim 1, wherein the NP is brain-type natriuretic peptide (NT-proBNP).

6. The method of claim 1, wherein the first time point is within 1 to 7 days of an onset of symptoms in the subject.

7. The method of claim 1, wherein the second time point is 2 to 14 days after the first time point.

8. The method of claim 1, wherein the MACE is selected from the group consisting of recurrence of an initial cardiac event; angina; decompensation of heart failure; admission for cardiovascular disease (CVD); mortality due to CVD; and transplant.

9. The method of claim 1, wherein the subject has been diagnosed with heart failure.

10. The method of claim 1, wherein the reference MACERS is a MACERS of a subject or group of subjects having a low risk of a MACE within one year.

11. The method of claim 1, wherein the biological sample obtained at the first time point or the biological sample obtained at the second time point comprises serum, blood, plasma, or urine.

12. The method of claim 1, wherein the reference MACERS is about 3.2, and a MACERS that is greater than or equal to the reference MACERS indicates that the subject has an elevated risk of a MACE within one year, compared to a subject with a MACERS below the reference MACERS.

13. The method of claim 1, wherein the subject has a body mass index (BMI) of 25 to 29, a BMI of greater than or equal to 30, or impaired renal function.

14. The method of claim 1, wherein a decision to discharge the subject or to continue treating the subject on an inpatient basis is made based in part on the MACERS.

15. The method of claim 1, wherein the biological samples are obtained from a subject that has been hospitalized after having an acute cardiac event.

16. The method of claim 1, wherein the subject has a pulmonary disorder or a liver disorder.

17. The method of claim 16, wherein the pulmonary disorder is acute infection, chronic obstructive pulmonary disease, or pulmonary embolism.

18. The method of claim 16, wherein the liver disorder is a liver disorder associated with chemotherapy, alcohol toxicity, or drug toxicity.

* * * * *